(12) United States Patent
Melman

(10) Patent No.: US 11,213,268 B2
(45) Date of Patent: *Jan. 4, 2022

(54) X-RAY SYSTEM WITH COMPUTER IMPLEMENTED METHODS FOR IMAGE PROCESSING

(71) Applicant: CONTROLRAD SYSTEMS INC., Radnor, PA (US)

(72) Inventor: Haim Zvi Melman, Kfar Saba (IL)

(73) Assignee: CONTROLRAD, INC., Peachtree Corners, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/009,838

(22) Filed: Sep. 2, 2020

(65) Prior Publication Data

US 2020/0397395 A1 Dec. 24, 2020

Related U.S. Application Data

(63) Continuation of application No. 15/757,985, filed as application No. PCT/IB2016/055344 on Sep. 8, 2016, now Pat. No. 10,820,875.

(Continued)

(51) Int. Cl.
*A61B 6/00* (2006.01)
*G06T 5/40* (2006.01)
(Continued)

(52) U.S. Cl.
CPC ............. *A61B 6/5205* (2013.01); *A61B 6/06* (2013.01); *A61B 6/542* (2013.01); *G06T 5/009* (2013.01);
(Continued)

(58) Field of Classification Search
CPC ......... A61B 6/5205; A61B 6/542; A61B 6/06; G06T 5/40; G06T 5/009; G06T 2207/20208; G06T 2207/10116
See application file for complete search history.

(56) References Cited

U.S. PATENT DOCUMENTS 6,850,642 B1 2/2005 Wang
10,820,875 B2 * 11/2020 Melman ............... A61B 6/5205
(Continued)

FOREIGN PATENT DOCUMENTS

WO 2014106783 A1 7/2014

OTHER PUBLICATIONS

International Search Report in PCT/IB2016/055344 dated Dec. 6, 2016.

*Primary Examiner* — Marcus H Taningco
(74) *Attorney, Agent, or Firm* — Manelli Selter PLLC; Edward Stemberger

(57) ABSTRACT

An x-ray system includes an x-ray source, at least one partially transparent x-ray filter, an x-ray detector, a monitor to display x-ray images detected by the detector and image processing. The display includes a dynamic range. The system is configured to generate at least one x-ray image and modify at least one of the at least one image for display by: using the at least one filter to filter x-ray so as to reduce x-ray intensity in at least one part of the image; maintaining at least one part of the image unfiltered by the at least one filter; determining a range in the dynamic range of the display; and modifying at least one pixel in the at least one filtered part of the image based on the determined range of the dynamic range of the display.

8 Claims, 13 Drawing Sheets

Related U.S. Application Data

(60) Provisional application No. 62/215,789, filed on Sep. 9, 2015.

(51) Int. Cl.
*G06T 5/00* (2006.01)
*A61B 6/06* (2006.01)

(52) U.S. Cl.
CPC ...... *G06T 5/40* (2013.01); *G06T 2207/10116* (2013.01); *G06T 2207/20208* (2013.01)

(56) References Cited

U.S. PATENT DOCUMENTS

| | | | | |
|---|---|---|---|---|
| 2006/0008174 A1* | 1/2006 | Avinash | .................. | G06T 5/002 382/275 |
| 2012/0219203 A1* | 8/2012 | Adachi | ................ | H04N 5/3651 382/132 |

* cited by examiner

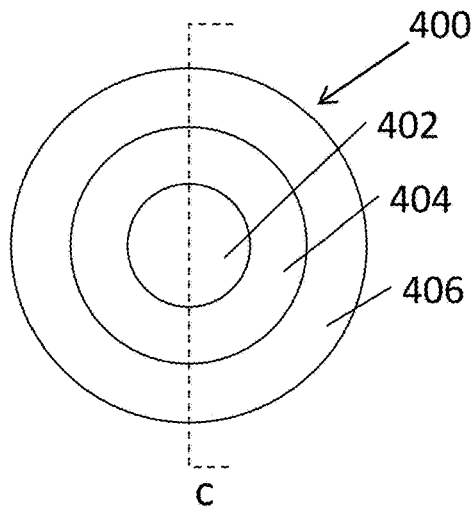
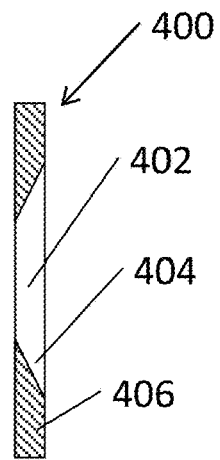
Figure 4A    Figure 4B
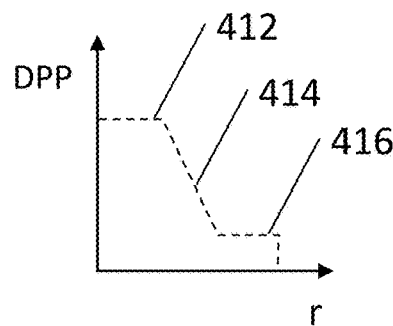
Figure 4C
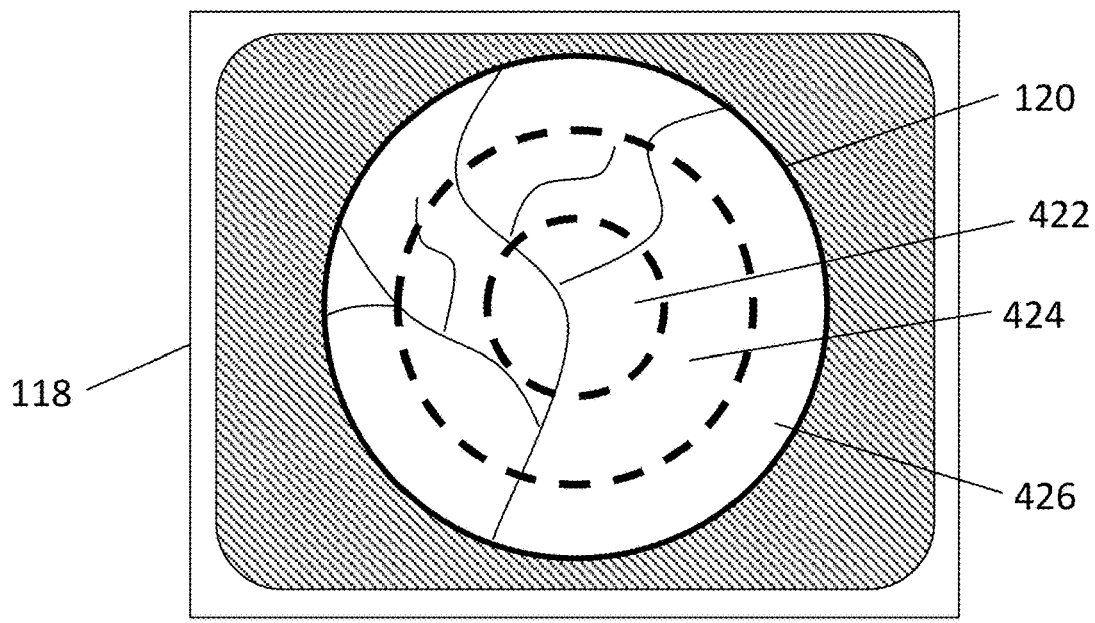
Figure 4D

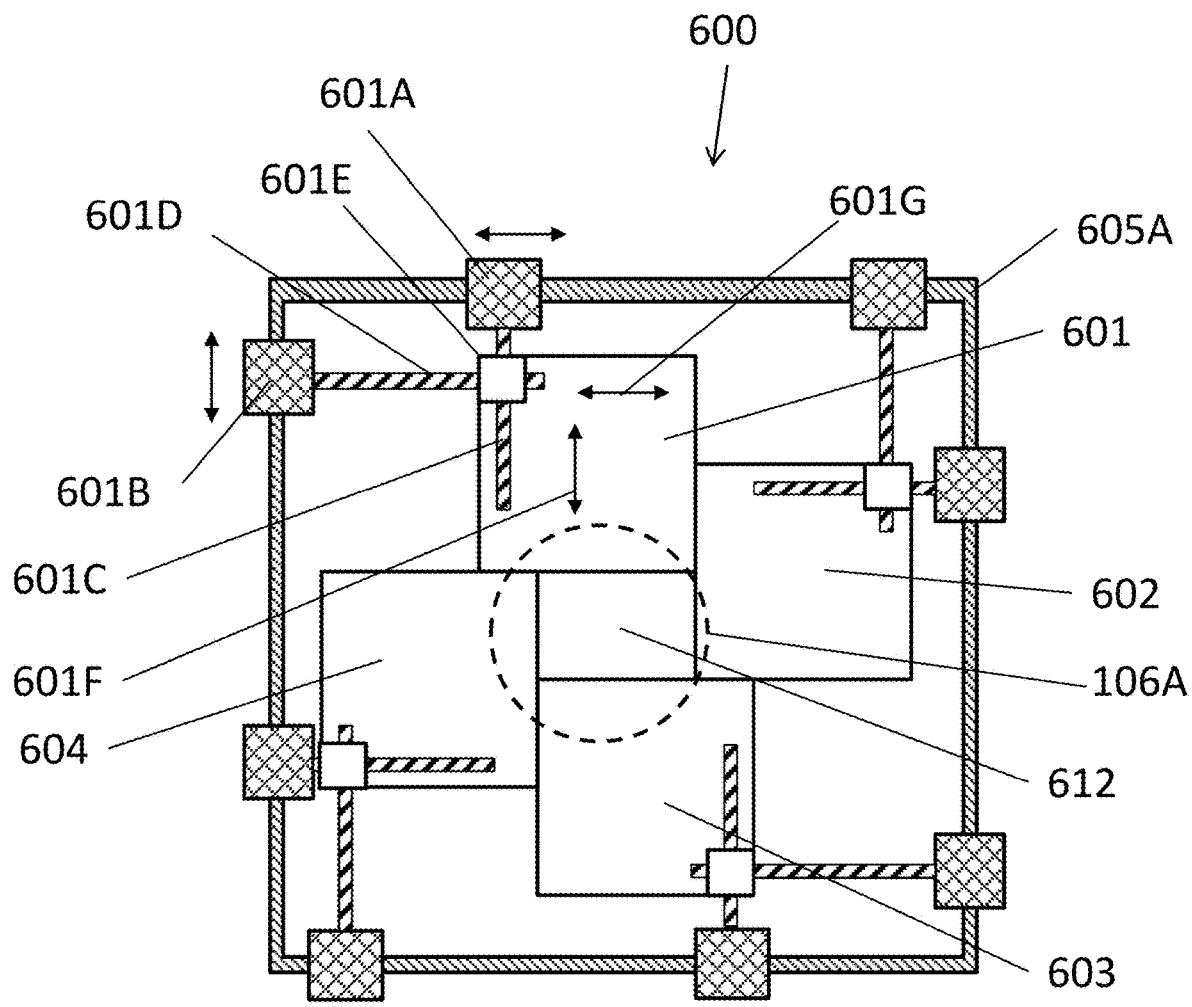
Figure 6
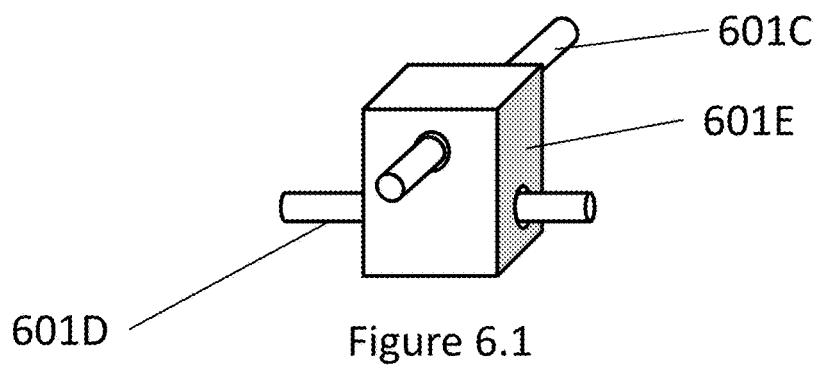
Figure 6.1

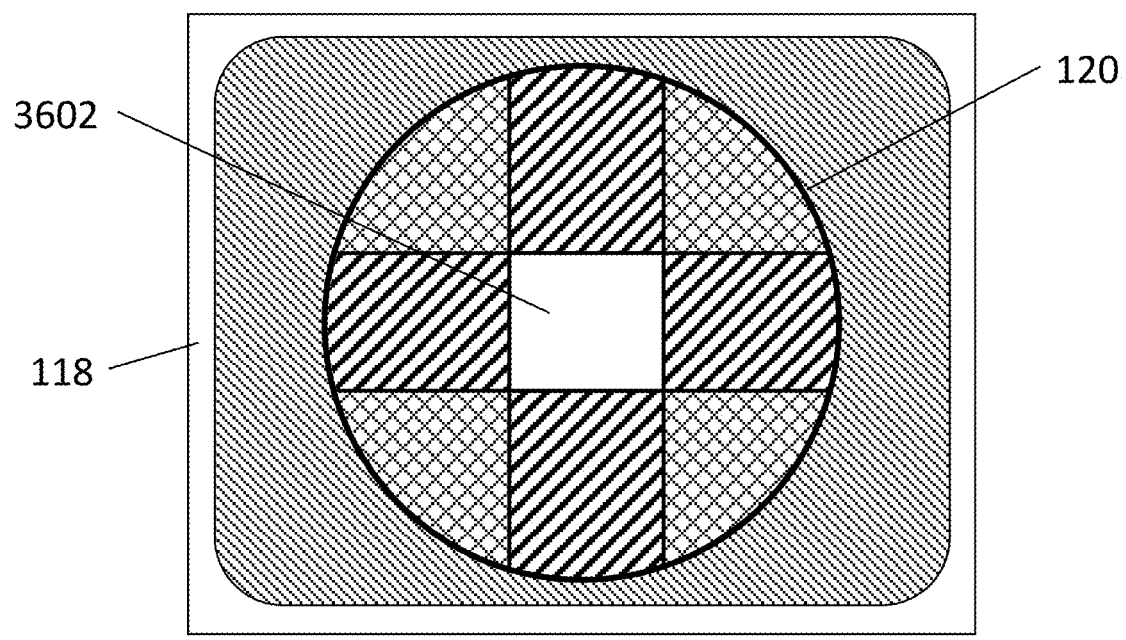
Figure 6.2

X-RAY SYSTEM WITH COMPUTER IMPLEMENTED METHODS FOR IMAGE PROCESSING

CROSS-REFERENCE TO RELATED PATENT APPLICATIONS

This application is a continuation of U.S. application Ser. No. 15/757,985, filed on Mar. 7, 2018, which is 371 of PCT/IB2016/055344, filed on Sep. 8, 2016, which claims the benefit of U.S. Provisional Application No. 62/215,789, filed on Sep. 9, 2015.

FIELD OF THE INVENTION

The invention is related to the field of imaging systems and more particularly to the field of image processing in images of x-ray systems involving a filter based region of interest.

BACKGROUND OF THE INVENTION

Although the present invention is applicable to various imaging system, it will be described in reference to fluoroscopy x-ray systems that incorporate filters for reducing radiation in a part of the field of view (FOV).

Devices and system that generate various forms of radiation/ionizing energy are used for various therapeutic/treatment, diagnostic or imaging purposes. For example, various forms of radiation/ionizing energy may be used to inspect an object (such as in airports scanning systems, different security setups, manufacturing and process control) or inspect a patient (such as in a clinic or a hospital, e.g. Cath lab, where a surgeon/therapist operates an X Ray or CT system.)

The medical imaging industry for example is heavily focused on reducing the radiation dose in diagnostic and treatment procedure that include hardware and software modification and operator room procedures. See Miller D L, Balter S, Schueler B A, Wagner L K, Strauss K J, Vano E. "Clinical radiation management for fluoroscopically guided interventional procedures", *Radiology*. November 2010; 257 (2):321-332. The reporting of radiation dose is one of the QA measurements that are required by Medicare. Furthermore, the Food and Drug Administration in their 2010 "White paper" called for significant reduction of the "unnecessary radiation". FDA, "White Paper: Initiative to Reduce Unnecessary Radiation Exposure from Medical Imaging. In: Administration CfDaRHUSFaD, ed. 2010.

There are two main components that can reduce radiation exposure. The first component is the technical improvements of the x-ray equipment, such as investment in better filtering, collimators, acquisition equipment and image analysis. The other component is the way the operator uses the radiation, which includes the length of exposure, distance from the source to the patient and proper collimation. See Miller D L, Balter S, Schueler B A, Wagner L K, Strauss K J, Vano E. "Clinical radiation management for fluoroscopically guided interventional procedures", *Radiology*. November 2010; 257(2):321-332 and Arthur W R, Dhawan J, Norell M S, Hunter A J, Clark A L, "Does cardiologist- or radiographer-operated fluoroscopy and image acquisition influence optimization of patient radiation exposure during routine coronary angiography?", *Br J Radiol*. September 2002; 75(897):748-753. The radiation education of the operator/physician is critical to reduce the radiation dose and trained physician utilize significantly lower amounts of radiation. A similar focus to reduce radiation exposure exists in the non-medical areas. For example, the nuclear industry has been very sensitive for several decades to radiation exposure and in many other manufacturing fields there are strict guidelines for minimizing exposure. See Http://www.state.il.us/iema/publications/pdf/IEMA %20032%20Everyday%20Uses%20of%20Radiation.pdf.

For example, during a fluoroscopy guided, interventional medical procedure, there are periods of time when the operator (usually a physician), even when he/she activates the radiation source which radiates the patient and the staff does not receive the information that is generated by a radiation source. This radiation (and the information in it) are not only wasted but are furthermore needlessly damaging to the patient and the staff/operator of the radiation source. This may be referred to as "Unattended Radiation" (UR) which is undesirable. Thus, in the various different applications in which objects or patients are being inspected, it is desirable to reduce the Unattended Radiation and therefore minimize the exposure to the potentially harmful radiation by the operator and/or patient and it is to this end that the disclosure is directed.

SUMMARY OF THE INVENTION

According to a first aspect of the invention there is provided an x-ray system comprising an x-ray source, at least one partially transparent x-ray filter, an x-ray detector, a monitor to display x-ray images detected by said detector and image processing means, said system configured to generate at least one x-ray image and modify at least one of said at least one image for display by:
  using said at least one filter to filter x-ray so as to reduce x-ray intensity in at least one part of an image;
  maintaining at least one part of said image unfiltered by said at least one filter;
  determining a first gray level based on at least one of said at least one unfiltered part of said image;
  using at least one first gray level transformation function to transform the gray level of at least one first pixel of at least one of said at least one filtered image part to a gray level that is equal to or lower than said first gray level; and
  using at least one second gray level transformation function to transform the gray level of at least one second pixel of at least one of said at least one filtered image part to a gray level that is higher than or equal to said first gray level.

At least one of said first and second gray level transformation functions may be a monotonic increasing function.

At least one of said first and second gray level transformation functions may be selected from the group consisting of:
  (1) a linear function;
  (2) a polynomial function;
  (3) a logarithmic function;
  (4) an exponential function; and
  (5) any combination of the above functions.

At least one of said first and second gray level transformation functions may be a monotonic increasing function.

The system may further be configured to determine said first gray level using a method selected from the group consisting of:
  (1) a percentile of the histogram of the unfiltered by said at least one filter part of the image;
  (2) gray level of the pixel with the maximum gray level of the unfiltered by said at least one filter part of the image;

(3) selected based on the unfiltered by said at least one filter part of the image excluding outlier pixels; and
(4) selected based on the unfiltered by said at least one filter part of the image excluding a fixed number of pixels.

The system may further be configured to execute at least one of the following for each frame:
(1) determination of the first gray level;
(2) generation of the first gray level transformation function; and
(3) generation of the second gray level transformation function.

The system may further be configured to execute at most two of the following for each frame:
(1) determination of the first gray level;
(2) generation of the first gray level transformation function; and
(3) generation of the second gray level transformation function.

The system may further be configured to execute at least one of the following, following a detection of a predetermined level of change in a sequence of images:
(1) determination of the first gray level;
(2) generation of the first gray level transformation function; and
(3) generation of the second gray level transformation function.

The system may further be configured to calculate histograms of said images calculated as without filtering and following detection of a level of change in the images histograms brighter pixels, execute at least one of the following:
(1) determination of the first gray level;
(2) generation of the first gray level transformation function; and
(3) generation of the second gray level transformation function.

The system may further be configured to execute at least one of the following based on at least one image with the largest dynamic range among multiple frames:
(1) determination of the first gray level;
(2) generation of the first gray level transformation function; and
(3) generation of the second gray level transformation function.

The system may further be configured to execute at least one of the following based on at least one image with the largest dynamic range among a predetermined number of last frames:
(1) determination of the first gray level;
(2) generation of the first gray level transformation function; and
(3) generation of the second gray level transformation function.

The system may further be configured to execute at least one of the following based on at least one image with the largest dynamic range among frames received in a predetermined time range:
(1) determination of the first gray level;
(2) generation of the first gray level transformation function; and
(3) generation of the second gray level transformation function.

The system may further be configured to execute at least one of the following based on the average of at least two images with the largest dynamic range among multiple frames:
(1) determination of the first gray level;
(2) generation of the first gray level transformation function; and
(3) generation of the second gray level transformation function.

The system may further be configured to execute at least one of the following based on the average of at least two images with the largest dynamic range among a predetermined number of last frames:
(1) determination of the first gray level;
(2) generation of the first gray level transformation function; and
(3) generation of the second gray level transformation function.

The system may further be configured to execute at least one of the following based on the average of at least two images with the largest dynamic range among frames received in a predetermined time range:
(1) determination of the first gray level;
(2) generation of the first gray level transformation function; and
(3) generation of the second gray level transformation function.

The system may further be configured to execute at least one of the following based on a weighted average of past images:
(1) determination of the first gray level;
(2) generation of the first gray level transformation function; and
(3) generation of the second gray level transformation function.

The system may further be configured to execute at least one of the following based on a weighted average of past images:
(1) determination of the first gray level;
(2) generation of the first gray level transformation function; and
(3) generation of the second gray level transformation function; and wherein said system is further configured to reset said weighted average calculation when the latest image varies from said weighted average by more than a threshold.

The system may further be configured to execute at least one of the following based on a subset of received frames:
(1) determination of the first gray level;
(2) generation of the first gray level transformation function; and
(3) generation of the second gray level transformation function.

An operator may be configured to determine said at least one part of said image unfiltered by said at least one filter in real time.

The system may further be configured to determine said at least one part of the image unfiltered by said at least one filter in real time automatically.

The system may further be configured to determine said at least one part of the image unfiltered by said at least one filter using stored past history.

According to another aspect of the invention there is provided an x-ray system comprising an x-ray source, at least one partially transparent x-ray filter, an x-ray detector, a monitor to display x-ray images detected by said detector and image processing means, said system configured to generate at least one x-ray image and modify at least one of said at least one image for display by:
using said at least one filter to filter x-ray so as to reduce x-ray intensity in at least one part of said image;

maintaining at least one part of said image unfiltered by said at least one filter;
determining a first gray level based on at least one of said at least one unfiltered part of said image;
determining a second gray level based on the dynamic range of the monitor;
using at least one first gray level transformation function to transform a first gray level of at least one first pixel of at least one of said at least one filtered image part to a gray level that is equal to or lower than said first gray level; and
using at least one second gray level transformation function to transform a second gray level of at least one second pixel of at least one of said at least one filtered image part to a gray level that is higher than or equal to said first gray level and lower than or equal to said second gray level.

At least one of said first and second gray level transformation functions may be a monotonic increasing function.

At least one of said first and second gray level transformation functions may be selected from the group consisting of:
(1) a linear function;
(2) a polynomial function;
(3) a logarithmic function;
(4) an exponential function; and
(5) any combination of the above functions.

At least one of said first and second gray level transformation functions may be a monotonic increasing function.

The system may further be configured to determine said first gray level using a method selected from the group consisting of:
(1) a percentile of the histogram of the unfiltered by said at least one filter part of the image;
(2) gray level of the pixel with the maximum gray level of the unfiltered by said at least one filter part of the image;
(3) selected based on the unfiltered by said at least one filter part of the image excluding outlier pixels; and
(4) selected based on the unfiltered by said at least one filter part of the image excluding a fixed number of pixels.

The system may further be configured to execute at least one of the following, following a detection of a level of change in a sequence of images:
(1) determination of the first gray level;
(2) generation of the first gray level transformation function; and
(3) generation of the second gray level transformation function.

The system may further be configured to calculate histograms of said images calculated as without filtering and following detection of a level of change in the images histograms brighter pixels, execute at least one of the following:
(1) determination of the first gray level;
(2) generation of the first gray level transformation function; and
(3) generation of the second gray level transformation function.

The system may further be configured to execute at least one of the following based on at least one image with the largest dynamic range among frames received in a predetermined time range:
(1) determination of the first gray level;
(2) generation of the first gray level transformation function; and
(3) generation of the second gray level transformation function.

The system may further be configured to execute at least one of the following based on a weighted average of past images:
(1) determination of the first gray level;
(2) generation of the first gray level transformation function; and
(3) generation of the second gray level transformation function.

The system may further be configured to execute at least one of the following based on a weighted average of past images:
(1) determination of the first gray level;
(2) generation of the first gray level transformation function; and
(3) generation of the second gray level transformation function; and wherein said system is further configured to reset said weighted average calculation when the latest image varies from said weighted average more than a threshold.

According to another aspect of the invention there is provided an x-ray system comprising an x-ray source, at least one partially transparent x-ray filter, an x-ray detector, a monitor to display x-ray images detected by said detector and image processing means, said system configured to generate at least one x-ray image and modify at least one of said at least one image for display by:
using said at least one filter to filter x-ray so as to reduce x-ray intensity in at least one part of said image;
maintaining at least one part of said image unfiltered by said at least one filter;
determining at least one of GL(ref), GL(maxB), GL(maxC) GL(refC), GL(pC), GL(pD) and GL(highD);
based on at least one of said GL(ref), GL(maxB), GL(maxC) GL(refC), GL(pC), GL(pD) and GL(highD), determining at least one first gray level transformation function to transform the gray level of at least one first pixel of at least one of said at least one filtered image part; and
based on at least one of said GL(ref), GL(maxB), GL(maxC) GL(refC), GL(pC), GL(pD) and GL(highD), determining at least one second gray level transformation function to transform the gray level of at least one second pixel of at least one of said at least one filtered image part.

At least one of said at least one first and second gray level transformation functions may be a monotonic increasing function.

At least one of said at least one first and second gray level transformation functions may be selected from the group consisting of:
(1) a linear function;
(2) a polynomial function;
(3) a logarithmic function;
(4) an exponential function; and
(5) any combination of the above functions.

At least one of said at least one first and second gray level transformation functions may be a monotonic increasing function.

The system may further be configured to determine said at least one of GL(ref), GL(maxB), GL(maxC) GL(refC), GL(pC), GL(pD) and GL(highD) using a method selected from the group consisting of:
(1) a percentile of the histogram of the unfiltered by said at least one filter part of the image;

(2) gray level of the pixel with the maximum gray level of the unfiltered by said at least one filter part of the image;
(3) selected based on the unfiltered by said at least one filter part of the image excluding outlier pixels; and
(4) selected based on the unfiltered by said at least one filter part of the image excluding a fixed number of pixels.

The system may further be configured to execute at least one of the following, following a detection of a level of change in a sequence of images:
(1) determination of said at least one of GL(ref), GL(maxB), GL(maxC) GL(refC), GL(pC), GL(pD) and GL(highD);
(2) generation of the first gray level transformation function; and
(3) generation of the second gray level transformation function.

The system may further be configured to calculate histograms of said images calculated as without filtering and following detection of a level of change in said images histograms brighter pixels, execute at least one of the following:
(1) determination of said at least one of GL(ref), GL(maxB), GL(maxC) GL(refC), GL(pC), GL(pD) and GL(highD);
(2) generation of the first gray level transformation function; and
(3) generation of the second gray level transformation function.

The system may further be configured to execute at least one of the following based on at least one image with the largest dynamic range among frames received in a predetermined time range:
(1) determination of said at least one of GL(ref), GL(maxB), GL(maxC) GL(refC), GL(pC), GL(pD) and GL(highD);
(2) generation of the first gray level transformation function; and
(3) generation of the second gray level transformation function.

The system may further be configured to execute at least one of the following based on a weighted average of past images:
(1) determination of said at least one of GL(ref), GL(maxB), GL(maxC) GL(refC), GL(pC), GL(pD) and GL(highD);
(2) generation of the first gray level transformation function; and
(3) generation of the second gray level transformation function.

The system may further be configured to execute at least one of the following based on a weighted average of past images:
(1) determination of said at least one of GL(ref), GL(maxB), GL(maxC) GL(refC), GL(pC), GL(pD) and GL(highD);
(2) generation of the first gray level transformation function; and
(3) generation of the second gray level transformation function; and wherein said system is further configured to reset said weighted average calculation when the latest image varies from said weighted average more than a threshold.

According to another aspect of the invention there is provided an x-ray system comprising an x-ray source, at least one partially transparent x-ray filter, an x-ray detector, a monitor to display x-ray images detected by said detector and image processing means, wherein said display comprises a dynamic range;
said system configured to generate at least one x-ray image and modify at least one of said at least one image for display by:
using said at least one filter to filter x-ray so as to reduce x-ray intensity in at least one part of said image;
maintaining at least one part of said image unfiltered by said at least one filter;
determining a range in said dynamic range of said display; and
modifying at least one pixel in said at least one filtered part of said image based on said determined range of said dynamic range of said display.

The modification may be made by at least one gray level transformation function selected from the group consisting of:
(1) a linear function;
(2) a polynomial function;
(3) a logarithmic function;
(4) an exponential function; and
(5) any combination of the above functions.

A first gray level may be determined based on said unfiltered image; and
a second gray level may be determined based on said filtered image;
said at least one pixel of said filtered image may be transformed by a transformation so that said second gray level is changed relative to said first gray level; and
said transformation may maintain the gray levels of said filtered image within said determined range of said dynamic range of said display.

The difference between said first gray level and said second gray level after said transformation may be less than 25% of said determined range of said dynamic range of said display.

According to another aspect of the invention there is provided an x-ray system comprising an x-ray source, at least one partially transparent x-ray filter, an x-ray detector, a monitor to display x-ray images detected by said detector and image processing means, wherein said display comprises a dynamic range;
said system configured to generate at least one x-ray image and modify at least one of said at least one image for display by:
using said at least one filter to filter x-ray so as to reduce x-ray intensity in at least one part of said image;
maintaining at least one part of said image unfiltered by said at least one filter;
modifying the dynamic range of said at least one filtered part of said image to a first predetermined range of said display dynamic range; and
modifying the dynamic range of said at least one unfiltered part of said image to a second predetermined range of said display dynamic range.

The modification may be made by at least one gray level transformation function selected from the group consisting of:
(6) a linear function;
(7) a polynomial function;
(8) a logarithmic function;
(9) an exponential function; and
(10) any combination of the above functions.

A first gray level may be determined based on said unfiltered image; and a second gray level may be determined based on said filtered image;

said at least one pixel of said filtered image may be transformed by a transformation so that said second gray level is changed relative to said first gray level; and said transformations maintain the gray levels of said filtered and unfiltered images within their corresponding said determined ranges of said dynamic range of said display.

The difference between said first gray level and said second gray level after said transformations may be less than 25% of said dynamic range of said display.

BRIEF DESCRIPTION OF THE DRAWINGS

The invention will be better understood in reference to the following Figures:

FIG. 4A provides a top view of the collimator according to the present invention;

FIG. 4B is cross section c-c of the collimator of FIG. 4A;

FIG. 4C provides a schematic DPP graph as a function of distance from the center;

FIG. 4D provides a representation of a monitor with the displayed frame associated with the collimator of FIG. 4A;

FIGS. 6 and 6.1 provide a top view of a collimator/filter constructed of an example of four x-ray partially transparent plates;

FIG. 6.2 represents the x-ray cone cross section at generally the plane of collimator of FIG. 6;

DETAILED DESCRIPTION OF THE INVENTION

Although the present invention is applicable to various imaging system, it will be described in reference to fluoroscopy x-ray systems that incorporate filters for reducing radiation in a part of the field of view (FOV).

Throughout the following description reference is made to various collimators having plates or filters. Both terms are used in the same sense, to describe filters intended to change the intensity of the radiation in non-uniform manner over the Field of View (FOV), as opposed to filters intended for changing the spectrum of the radiation throughout the FOV.

Figure 1A:
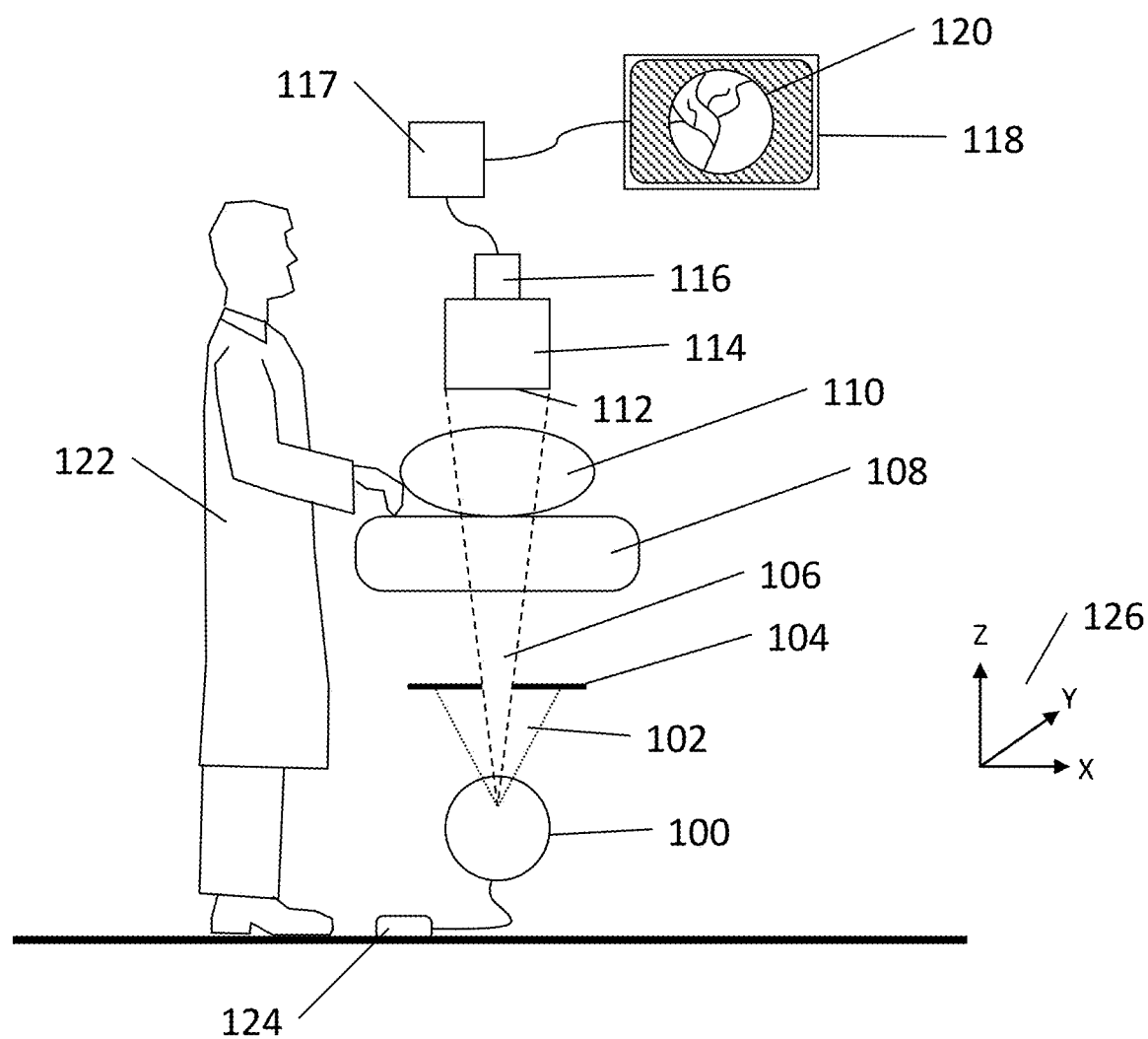
FIG. 1A is a simplified schematic illustration of an example layout of a multiple frames imaging clinical environment and system.

Reference is made now to FIG. 1A which presents a typical layout of a multiple frames imaging clinical environment, such as described in international patent application no. PCT/IB2013/051541, incorporated herein by reference.

X-ray tube 100 generates x-ray radiation 102 directed upward and covering a relatively large solid angle towards collimator 104. Collimator 104 blocks part of the radiation allowing a smaller solid angle of radiation to continue in the upward direction, go through bed 108 that is typically made of material that is relatively transparent to x-ray radiation and through patient 110 who is laying on bed 108. Part of the radiation is absorbed and scattered by the patient and the remaining radiation arrives at the typically round input area 112 of image intensifier 114. The input area of the image intensifier is typically in the order of 300 mm in diameter but may vary per the model and technology. The image generated by image intensifier 114 is captured by camera 116, processed by image processor 117 and then displayed on monitor 118 as image 120.

Although the invention is described mainly in reference to the combination of image intensifier 114 and camera 116 it would be appreciated that both these elements can be replaced by a digital radiography sensor of any technology such as CCD or CMOS flat panels or other technologies such as Amorphous Silicon with scintillators located at plane 112. One such example is CXDI-50RF Available from Canon U.S.A., Inc., Lake Success, N.Y. The term "detector" is used to include any of these technologies, including the combination of any image intensifier with any camera and including any type of a flat panel sensor or any other device converting x-ray to electronic signal.

The terms "area" and "region" are used alternatively in the detailed description of the invention and they mean the same and are used as synonyms.

The term "x-ray source" is used to provide a wide interpretation for a device having x-ray point source that does not necessarily have the shape of a tube. Although the term x-ray tube is used in the examples of the invention in convention with common terminology in the art, it is represented here that the examples of the invention are not limited to a narrow interpretation of x-ray tube and that any x-ray source can be used in these examples (for example even radioactive material configured to function as a point source).

Operator 122 is standing by the patient to perform the medical procedure while watching image 120.

The operator has a foot-switch 124. When pressing the switch, continuous x-ray radiation (or relatively high frequency pulsed x-ray as explained below) is emitted to provide a cine imaging 120. The intensity of x-ray radiation is typically optimized in a tradeoff of low intensity that is desired to reduce exposure to the patient and the operator and high intensity radiation that is desired to enable a high quality image 120 (high S/N). With low intensity x-ray radiation and thus low exposure of the image intensifier input area, the S/N of image 120 might be so low that image 120 becomes useless.

Coordinate system 126 is a reference Cartesian coordinate system with Y axis pointing into the page and X-Y is a plane parallel to planes such as that of collimator 104 and image intensifier input plane 112.

It is a purpose of the present invention to provide high exposure at the input area of the image intensifier in the desired one or more Regions of Interest (ROIs) that provide therefore a high S/N image there, while reducing the exposure of other sections of the image intensifier area, at the cost of lower image quality (lower S/N). With this arrangement the operator can see a clear image in the one or more ROIs and get a good enough image for general orientation in the rest of the image area. It is also a purpose of this invention to provide a more complex map of segments in the image where each segment results from a different level of x-ray radiation as desired by the specific application.

In the context of the examples provided throughout the detailed description of the invention, when S/N of one area is compared to S/N of another area the S/N are compared for pixels that have the same object (such as patient and operators hands and tools) transmittance. For example, when an area A is described as having lower S/N than area B it is assumed that the transmission of x-ray by the object to both areas is uniform over the area and is the same. For example, if at the center of the area A only ½ of the radiation arriving at the object is transmitted through to the image intensifier then, S/N in area B is compared to area A for an area B in which also only ½ of the radiation arriving at the object is transmitted through to the image intensifier. The S (signal) of area A is the average reading value of the area A (average over time or over the area if it includes enough pixels in the statistical sense). The S (signal) of area B is the average reading value of the area B (average over time or over the area if it includes enough pixels in the statistical sense). To simplify the discussion scattered radiation is not considered in the detailed description of the invention. The effect of scattered radiation and means to reduce it are well known in the art.

In the examples below the noise statistics is assumed to be of Gaussian distribution which satisfies most practical aspects of implementation of the invention and serves well clear presentations of examples of the detailed description of the invention. This is not a limitation of the invention and, if desired, the mathematics presented in association to Gaussian statistics can be replaced by that of Poisson statistics (or other statistics) without degrading the scope of the invention. The noise values associated with each signal are represented by the standard deviation of the Poisson statistics for that signal, known in the art as Poisson Noise.

Also dose per pixel (DPP) throughout the detailed description of the invention is discussed in the same sense, i.e. when the DPP of pixel A is compared to DPP of pixel B it is assumed the object transmission for both pixels is the same.

Figure 1B:
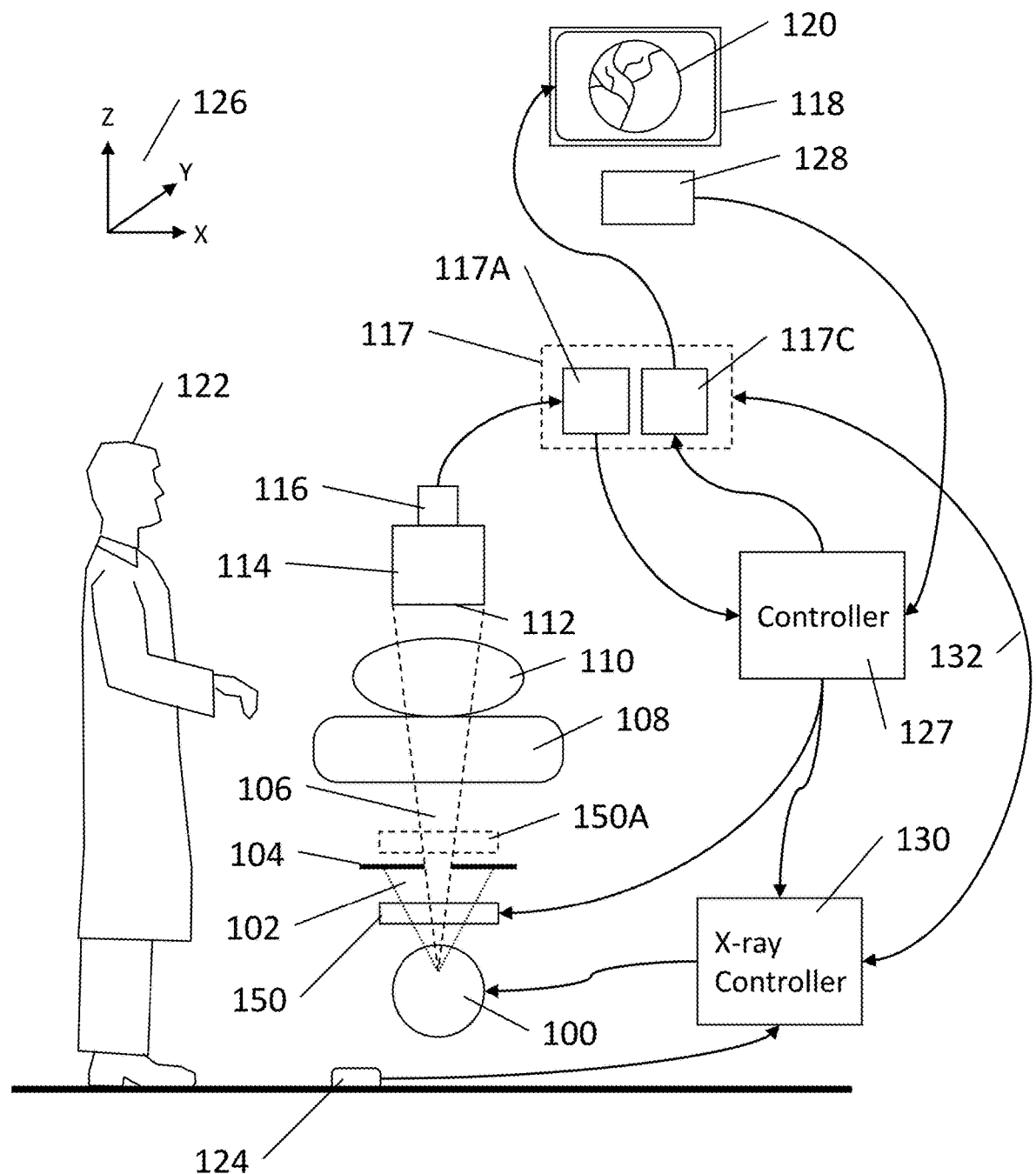
FIG. 1B is an illustration of an example of a layout of the system of FIG. 1A showing additional details of components of the system example of the invention.
Figure 10:
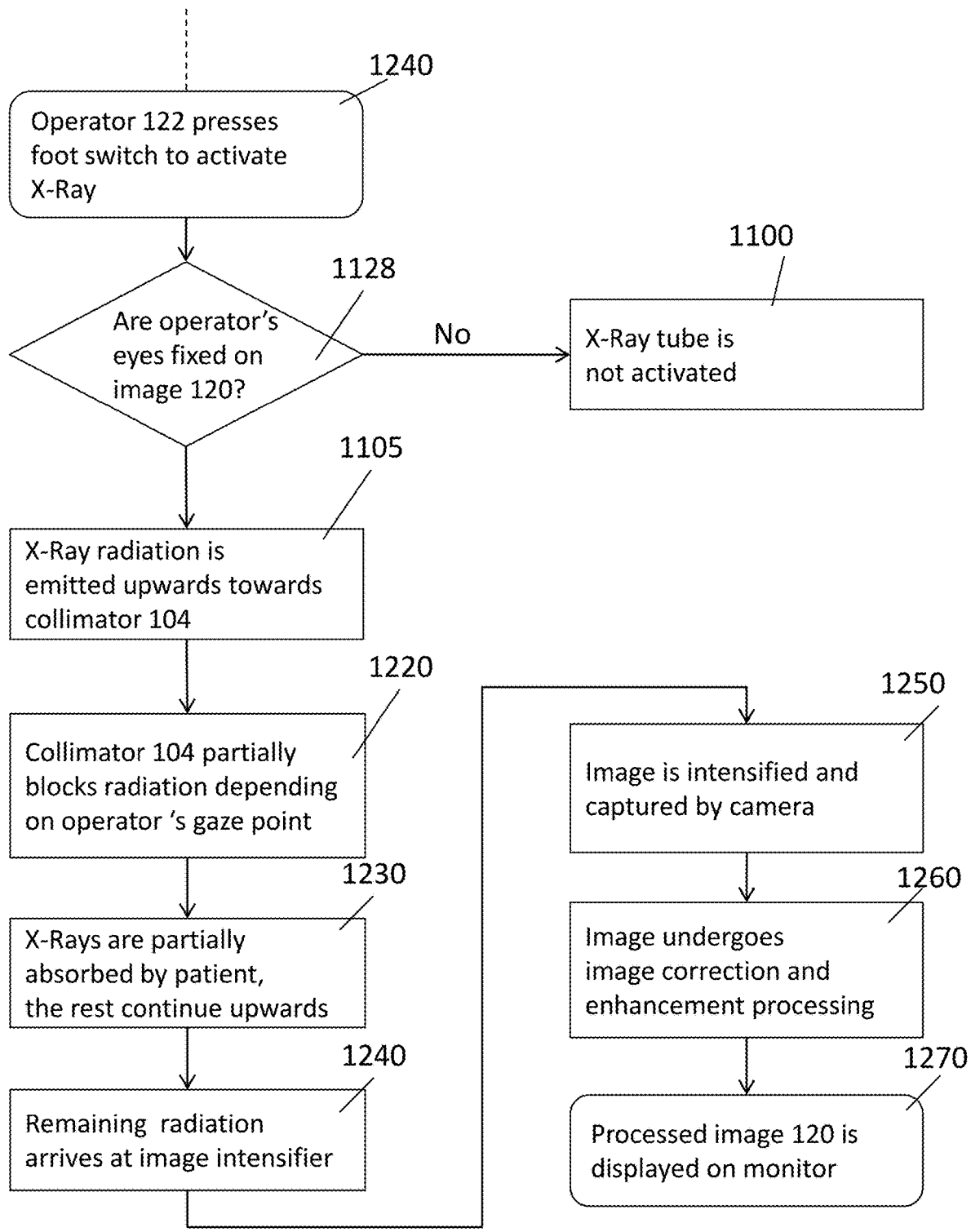
FIG. 10 is a flowchart showing the basic workflow of a system according to the present invention.

An example of a more detailed layout of a multiple frames imaging clinical environment according to the present invention is described in FIGS. 1B and 10. Operator 122 presses foot switch 124 to activate x-ray (step 1240). Eye tracker 128 (such as EyeLink 1000 available from SR Research Ltd., Kanata, Ontario, Canada) or any alternative input device provides indication where one or more operators (or users) 122 are focusing their attention (step 1128). This information is typically provided relative to monitor 118. This information, the at least one desired center of ROI, may be provided for example in terms of (X,Z) coordinates, in the plane of monitor 118, using coordinate system 126. It would be appreciated that in this example the plane of monitor 118 and therefore also image 120 are parallel to the (X,Z) plane of coordinate system 126. Other coordinate systems are possible, including coordinate systems that are bundled to monitor 118 and rotate with monitor 118 when it is rotated relative to coordinate system 126.

The data from input 128 is provided to controller 127 which is basically a computer, such as any PC computer. If the controller 127 determines that the operator's focus of attention is not fixed on the image 120, the x-ray tube 100 is not activated (step 1100). Otherwise, in step 1105, x-ray tube 100 is activated and x-ray radiation is emitted towards collimator 104 (and/or 150/150A).

Box 150 in FIG. 1B represents a collimator according to the present invention, as described in international patent application no. PCT/IB2014/065661 incorporated herein by reference.

Box 150 can be located under collimator 104, above collimator 104 as shown by numerical reference 150A or instead of collimator 104 (not shown in FIG. 1B). The collimators represented by boxes 150 and 150A are controlled by controller 127. X-ray emission is also controlled by controller 127, typically through x-ray controller 130. In one example, x-ray can be stopped even if operator 122 presses foot-switch 124 if at least one of the users' desired center of ROI is not within image 120 area. The collimator partially blocks radiation, depending on the determined at least one desired center of ROI (step 1220). Part of the x-rays are absorbed by the patient 110 (step 1230) and the remaining radiation arrives at the image intensifier 114 (step 1240). In step 1250 the image is intensified and captured by a camera 116 and in step 1260 the captured image is transferred to the image processor 117 and in step 1270 the processed image is displayed on monitor 120.

Figure 2:
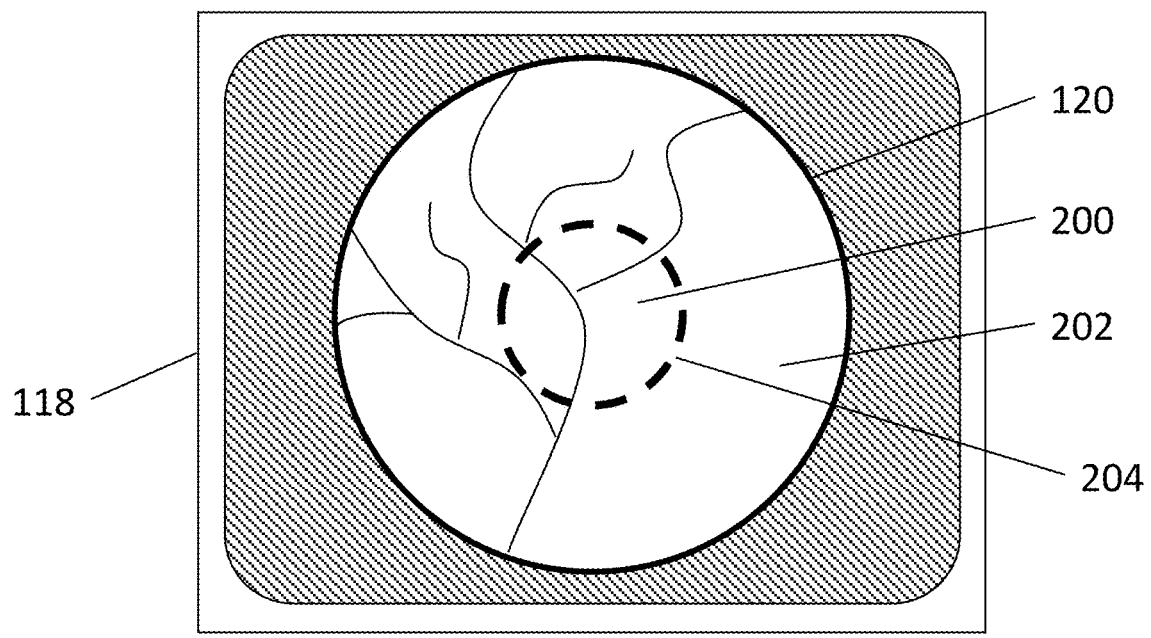
FIG. 2 is a schematic illustration of an example of image displayed on a monitor of a multiple frames imaging system.

Reference is made now to FIG. 2 illustrating an example of an image 120 displayed on monitor 118. In this example dashed circle line 204 indicates the border between segment 200 of the image and segment 202 of the image, both segments constitute the entire image 120. In this example it is desired to get a good image quality in segment 200, meaning higher x-ray DPP for segment 200 and it is acceptable to have a lower image quality in segment 202, meaning lower DPP for segment 202.

It would be appreciated that the two segments 200 and 202 are provided here only as one example of an embodiment of the invention that is not limited to this example and that image 120 can be divided to any set of segments by controlling the shape of the apertures in the collimators and the mode of motion of the collimators. Such examples are provided below.

It would be appreciated that DPP should be interpreted as the x-ray dose delivered towards a segment representing one pixel of image 120 to generate the pixel readout value used to construct image 120 (excluding absorption by the patient or other elements which are not a part of the system, such as the hands and tools of the operator).

Figure 3:
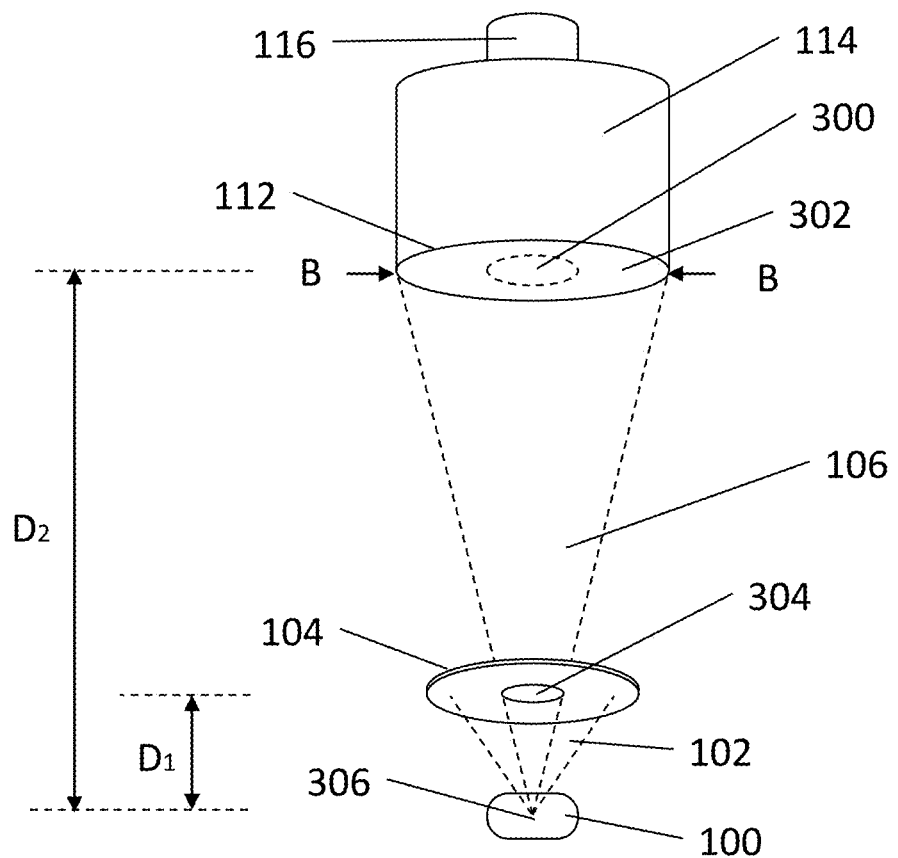
FIG. 3 is a schematic illustration of additional aspects of the system example of FIG. 1A.

Reference is made now to FIG. 3. A typical collimator 104 having a round aperture 304 is introduced to the x-ray path so that only x-rays 106 that are projected from focal point 306 of x-ray tube 100 and pass through aperture 304 arrive at the round input surface 112 of image intensifier 114 while other x-rays 102 are blocked by the collimator. This arrangement exposes the entire input area 112 of the image intensifier to generally the same DPP. Such an arrangement does not provide the function of one DPP to segment 300 that correlates with segment 200 of FIG. 2 and another DPP to segment 302 that correlates with segment 202 of FIG. 2. The diameter of input area 112 is B as indicated in FIG. 3.

D1 represents the distance from the x-ray focal point 306 to aperture 304. D2 represents the distance from the x-ray focal point 306 to image intensifier input surface 112.

FIG. 4A provides a top view of another collimator 400 and FIG. 4B is cross section c-c of FIG. 4A. Collimator 400 provides a similar function of x-ray reduction as other collimators of the invention. It has an aperture 402 that allows all the radiation in that area to pass through, annulus 406 that reduces the radiation passing through the area at amount depending on the material (typically aluminum) and the thickness of the material and annulus 404 with thickness changing as a function of the distance from the center, starting at thickness zero on the side of aperture 402 ending at the thickness of annulus 406 on the side of annulus 406. FIG. 4C provides a schematic DPP graph as a function of distance from the center: r.

FIG. 4D provides a representation of monitor 118 with the displayed frame associated with collimator 400. Circle 422 is the area associated with radiation arriving through aperture 402 of collimator 400. Annulus 424 is the area associated with radiation arriving through annulus 404 of collimator 400. Annulus 426 is the area associated with radiation arriving through annulus 406 of collimator 400. It would be appreciated that while the example of annulus 404 in FIG. 4B is linear change of thickness, the example of change in radiation of 414 in FIG. 4C is of a non-linear thickness change. That is, many different functions can be used to generate gradient in thickness 404 to suit the desired gradual change in radiation between aperture 402 and annulus 406 of FIG. 4B.

Figure 5:
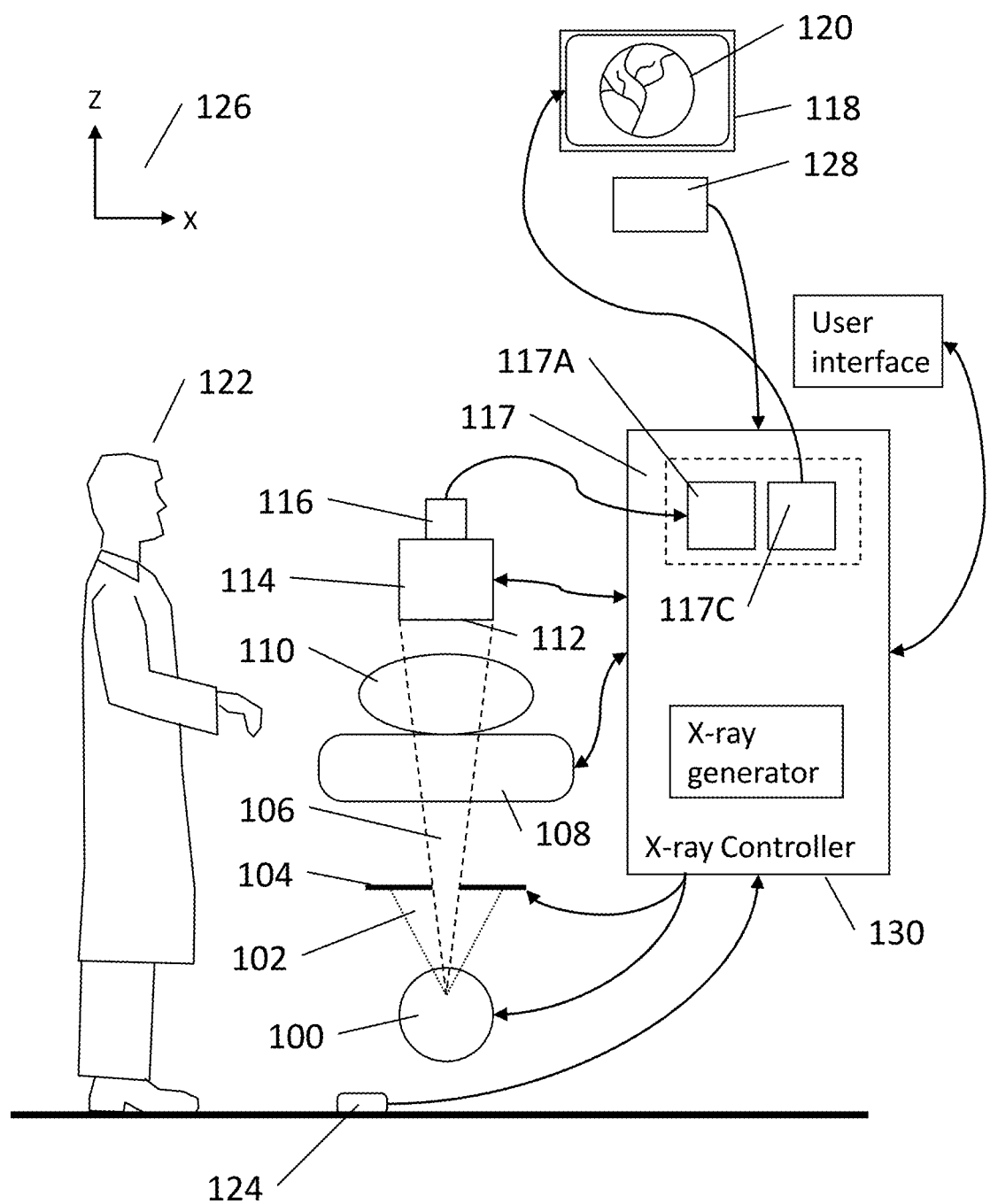
FIG. 5 presents an exemplary system for carrying out the invention.

Attention is drawn now to FIG. 5 which presents an exemplary system for carrying out the invention.

Typically in x-ray systems, an ROI is centered in image 120 (such as ROI 200 of FIG. 2) and has a fixed position which is used for image analysis and for generating parameters to drive x-ray tube 100 and modify image 120. Parameters such as average value, maximum value and contrast may be calculated for this area. Such parameters are typically used to optimize the x-ray tube operation (such as mA, mAs and KVp).

In this example an input device such as an eye tracker 128 is used to provide x-ray controller 130 with the focus of attention coordinates of one or more users 122. Instead of using a fixed position ROI as in the prior art, the one or more ROIs move according to the focus of attention so that they include the desired centers of the ROIs or are near the desired centers of the ROIs. With this adjustment of the ROIs position as a function of the focus of attention, the analysis and parameters calculated from the ROIs to drive the x-ray tube and modify image 120 are made from at least one ROI that is located according to the focus of attention instead of a fixed ROI, that may sometimes be at a distance from the focus of attention and not represent the image information that is relevant to the focus of attention.

In the example of FIG. 5, the input device can be any input device that affects the position and/or the shape of the ROI. For example, an eye tracker, a joy-stick, a keyboard, an interactive display, a gesture reading device, a voice interpreter or any other suitable device can be used to determine coordinates relative to image 120, and the ROI position and/or shape changes according to such input.

Reference is made now to FIGS. 6, 6.1 and 6.2 providing another exemplary collimator 600, such as described in international patent application no. PCT/IB2014/065661 incorporated herein by reference. Collimator 600 comprises four plates 601, 602, 603 and 604 that are opaque or partially transparent to x-ray. In this example we shall assume that each such plate transmits 10% of beam 106 but it would be appreciated that other transmission levels may be contemplated. Plates 601, 602, 603 and 604 can be made from any suitable material, considering the desired effect of the spectral distribution of the transmitted x-ray beam. For example, copper or aluminum plates can be used.

Dashed circle 106A represents x-ray cone 106 cross section at generally the plane of collimator 600. Except for a rectangular shaped x-ray beam portion 612, the rest of the beam intensity is reduced due to plates 601, 602, 603 and 604.

It is appreciated that a circular image/circular cone shape x-ray beam is only an example. The x-ray beam and the image may be rectangular or any other shape, depending on the c-arm and collimator setup.

With this example of collimator 600 therefore ROI 3602 of image 120 (FIG. 6.2) cannot only be moved across the area of image 120 to the desired location but also the size and aspect ratio of the ROI can be changed as desired, to compensate for zoom in image intensifier 114 (FIG. 1A) or for other reasons.

Figure 7:
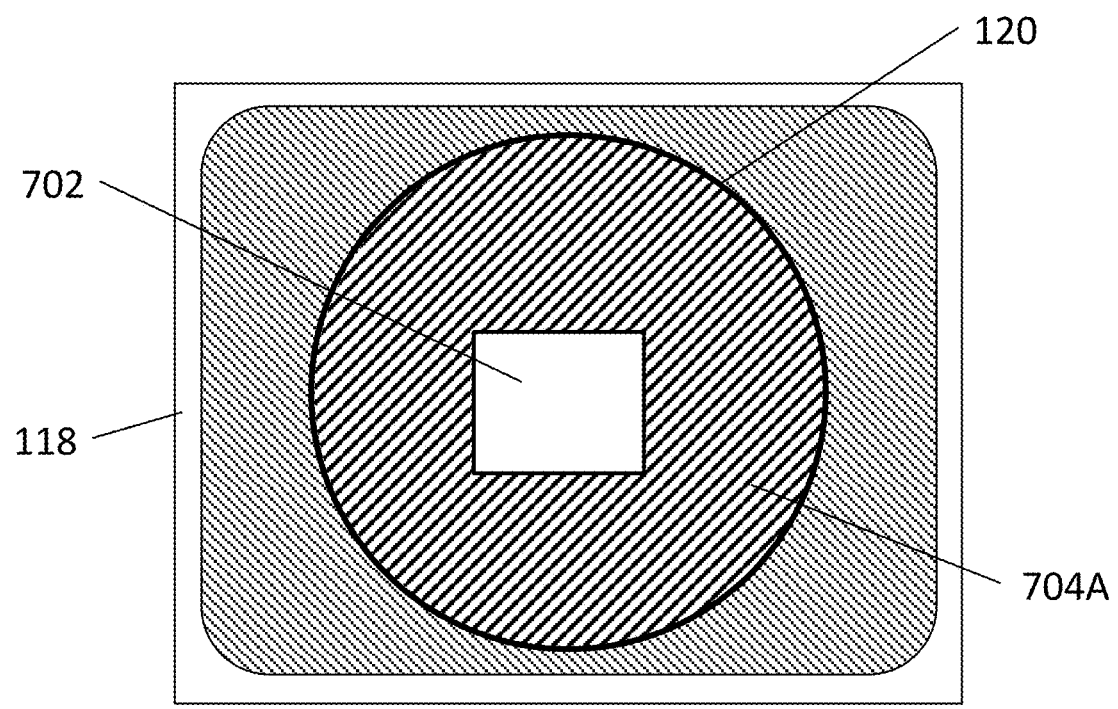
FIG. 7 illustrates the x-ray intensity distribution in different areas of the image of the collimator/filter of FIG. 6 at an example position.

Reference is made now to FIG. 7, illustrating the x-ray intensity distribution in different areas of image 120 when the image ROI 702 is in the position resulting from mechanical ROI 612 presented in FIG. 6. In this example there is no object (patient) between collimator 600 and input area 112 so, ideally, without additional conventional collimator blocking radiation, the x-ray radiation over input area 112, outside of the ROI, would be uniform (up to specific system inherent uniformity limitations). In this example, as a result of collimator 600 the area of image 120 is divided into two intensity areas: 702, the ROI, where the original 100% intensity is and 704 where the intensity is 10% of that at the ROI.

The present invention is described in reference to utilizing partially transparent filters deployed between the radiation source and the object (typically a patient) to reduce radiation in at least a part of the image, such as in the examples of FIG. 6 and resulting images such as in the example of FIG. 7, but it will be appreciated that the invention is not limited to these filters but it is also fully applicable to collimators/filters such as in the example of FIGS. 4A-4B and resulting images such as in the example of FIG. 4D. In fact, this invention is applicable to any x-ray system using filters that are partially transparent, for example in the transparency range of 1% to 99%, and typically in the range 5% to 70%.

Figure 8A:
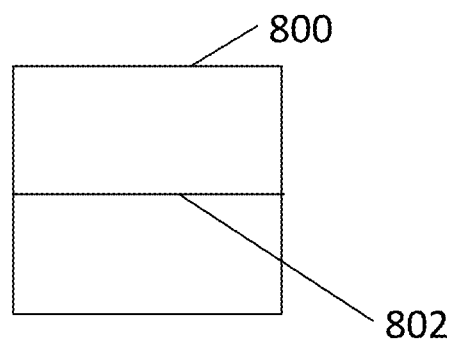
FIG. 8A shows an image or detector area represented as a rectangle with one image line.

Reference is made to FIG. 8A. Image or detector area 800 is represented as a rectangle. The following explanation will refer to an x-ray image displayed on a monitor such as 118 of FIG. 1B, but it would be appreciated by those skilled in the art that an explanation referring to an x-ray detector, whether a flat panel detector of an image intensifier, is analogous. Line 802 represents one line of the image, an "image line". In this example image line 802 is at the center of image 800.

Figure 8B:
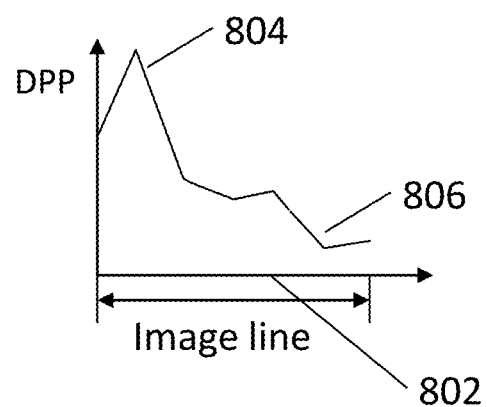
FIG. 8B is an example of DPP distribution along the image line of FIG. 8A at the detector.

FIG. 8B is an example of DPP distribution along image line 802 at the detector. High DPP 804 will be the result of relatively transparent parts of the patient 110 of FIG. 5 (or inspected object) and low DPP 806 will be the results of relatively opaque parts of the patient 110 of FIG. 5 (or inspected object, hereafter: the patient). For example, high DPP 804 may be present due to relatively transparent lungs and low DPP 806 may be present due to relatively opaque heart. In another example high DPP 804 may be present due to clear air just outside a patient's leg and low DPP 806 may be present due to relatively the opaque leg of the patient. Such situations present high dynamic range of the image, meaning that the ratio between the high DPP of the image and the low DPP is high.

Figure 8C:
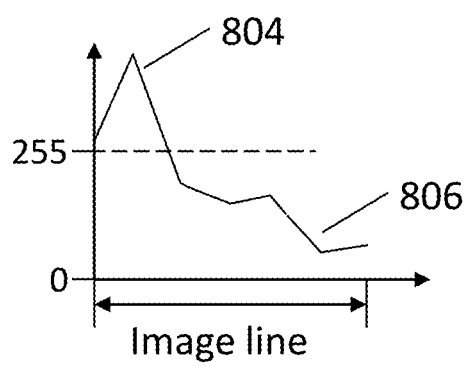
FIG. 8C represents a display system having 256 gray levels.
Figure 8D:
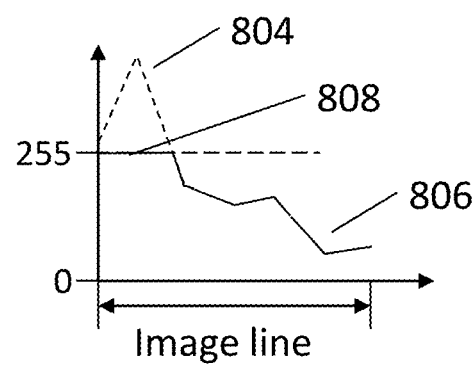
FIG. 8D shows the details of the image line compressed to a flat gray level 255.

Such a situation often creates problems in displaying the entire dynamic range of the image as shown in FIG. 8C and FIG. 8D.

FIG. 8C represents a display system having 256 gray levels (an 8 bit system).

It would be appreciated that the invention is not limited to 8 bit system and this is used only as an example to facilitate the description of the invention.

The vertical axis represents here the gray levels. Enough x-ray (and suitable image processing) are provided to display 806 part of the image in a suitable brightness and contrast. This however, "pushes" part 804 beyond the dynamic range of the display system, beyond gray level 255. The result is demonstrated in FIG. 8D. The details of 804 are compressed to a flat gray level 255 as shown by numerical indicator 808. Image part 804 is displayed then with no details, a white washed-out area.

Figure 9A:
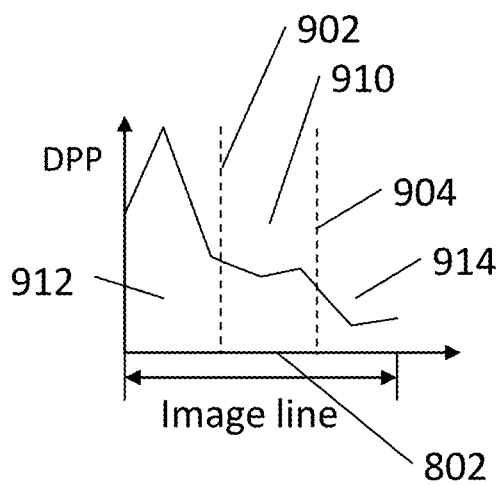
FIG. 9A is an example of the image line of FIG. 8B where added dashed lines indicate the borders between 3 parts of the image.
Figure 9B:
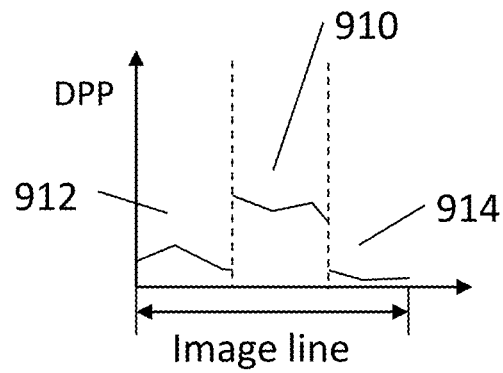
FIG. 9B shows the reduced DPP in the backgrounds and the unchanged DPP in the ROI.
Figure 9C:
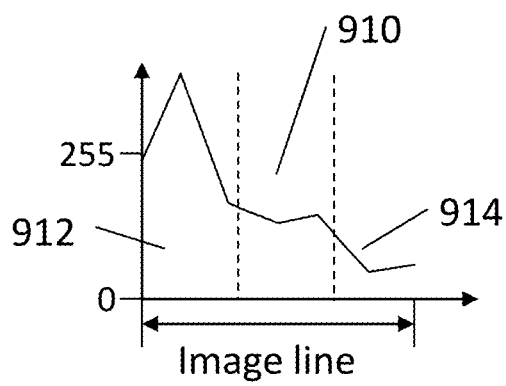
FIG. 9C shows a corrected image of FIG. 9B so as to restore the image to what it would have been without filtering.
Figure 9D:
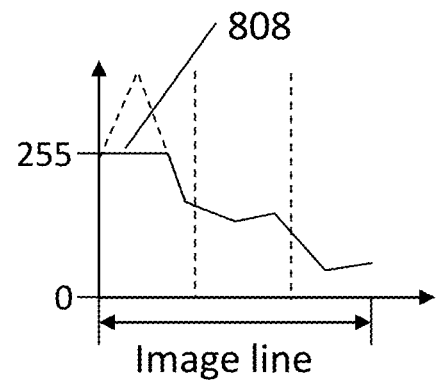
FIG. 9D shows the result as a washed out part of the image that has no image details.

When using filters as described above, at least a part of the image area receives a reduced DPP, a reduced radiation. FIG. 9A is an example of image line 802 of FIG. 8B where added dashed lines 902 and 904 indicate the borders between 3 parts of the image: image part 910 (ROI), 912 (background) and image part 914 (background). In this example, backgrounds 912 and 914 are filtered to reduce DPP and ROI 910 is not filtered. The result is illustrated in FIG. 9B, showing the reduced DPP in backgrounds 912 and 914 and the unchanged DPP in ROI 910. Methods disclosed in the reference inventions teach correcting the reduced DPP parts of the image to generally resemble the image that would have been displayed when not using the filters to reduce DPP in the background. Correcting such an image with a high dynamic range, so as to restore the image to what it would have been without filtering would make the corrected image data of FIG. 9B look like in FIG. 9C, where much of the data in image part 912 exceeds the maximum display range and therefore is clipped to a single gray level 255, as shown in FIG. 9D by numerical indicator 808. This will result is a washed out part of the image that has no image details.

To resolve this situation a computer implemented method is provided to process the background (filtered parts such as 912 and 914) so as to avoid washed out parts of the image (i.e. a part of the image that becomes all flat white and details are lost).

In one example different image parts are evaluated for brightening the image based on a brightest percentile of each part. For example, for each part a histogram is calculated and the gray level of selected percentile (histogram population percentile) is identified. The brightening of this image part is made so that the gray level of this percentile is transformed to a desired gray level.

In one example the percentile may be selected a 90%. A transformation of the gray levels of the processed image part may be specified to transfer this 90% gray level to display level of 225 (out of the 256 gray levels of the example system). The brightening function may be any tone reproduction function (also referred to herein as transformation, transformation function, gray level transformation and gray level transformation function) such as a factor multiplying each gray level of the original pixel to get the desired pixel value. In such a transformation, if for example the 90% percentile gray level is 150 and the desired display gray level (Target gray level) for this percentile is 225, the transformation factor will be 225/150=1.5.

Figure 9E:
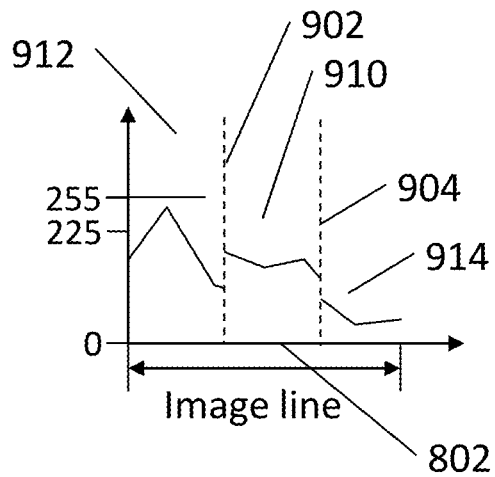
FIG. 9E shows the result after applying a basic background processing.

Such a basic background processing may produce the result illustrated in FIG. 9E. It is appreciated that in this specific example, the 90% percentile gray level in background 912 is transformed to gray level 225. In this example also the percentile range between 90% to 100% of background 912 is below gray level 255 and therefore there is no washed out parts of the image and all details are visible.

In this example, note the possibility of discontinuity result of the image along image line 802, at the location of border lines 902 and 904 demonstrated in FIG. 9E.

An exemplary alternative to a simple multiplication factor may be a general linear function of any degree. In the following example, a first degree linear function is demonstrated, with a multiplication factor and offset factor in the form:

$$\text{New\_GL}(Pi) = \text{Original\_GL}(Pi) \cdot \text{Factor} + \text{Offset}$$

Where for each pixel i:

Original_GL(Pi) is the original gray level of pixel i (after filtering);

Factor in the multiplication factor;

Offset is the offset constant; and

New_GL(Pi) is the new pixel gray level following the transformation.

Figure 9F:
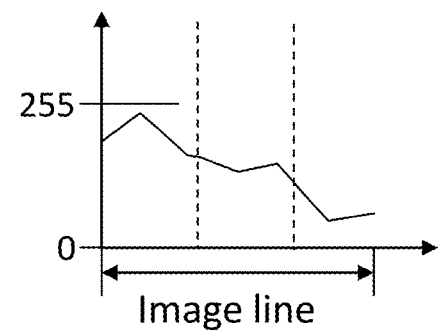
FIG. 9F shows providing continuity of the image along the image line of FIG. 8B, at the location of the border lines.

This approach can support providing continuity of the image along image line 802, at the location of border lines 902 and 904, as demonstrated in FIG. 9F.

Additional transformation such as Gamma, logarithmic or any other transformation can be used where typically all such transformations are monotonic increasing functions.

It would be appreciated that 90% histogram percentile can be replaced by the brightest pixel that is equivalent to 100% percentile, by an outliers (such as in statistics, an outlier is an observation point that is distant from other observations) ignoring outlier pixels in the histogram or by ignoring a fixed number of the brightest pixels instead of using percentile.

It would also be appreciated that the target number may be below the maximum displayable gray level (such as 225 out of 255 in the above example), or it may be the maximum displayable gray level or above the maximum displayable gray level. All depends on the desired user experience and thereby on the specific implementation.

In another example the transformation can be designed to prevent the discontinuity presented in reference to FIG. 9E. This will be described below in reference to a linear system where the gray level of a pixel is directly proportional to the DPP for that pixel. It would be appreciated by those skilled in the art that if the processing is done for a non-linear data, such as logarithmic, a multiplication by factor provided as an example below would become an additive constant and that similar adjustments should be done, depending on possible pre-processing of the image before being handled according to the present invention.

Also, in this example a requirement is set to transform the 90% percentile gray level of the background to gray level 225 of the display system, but in this example more constrains are added and used for the processing of the background as in the following example process:

1. The background image is processed according to the previous references so as to provide an image as if no radiation was reduced by the filters of the invention. This will provide the background gray levels (calculated, not displayed) of FIG. 9C (912 and 914).

In this example it is assumed that the background image is processed using a multiplication factor F. The calculated gray level of pixel i in the processed background is CBKG_GL(*Pi*)=BCK_GL(*Pi*)·F where BCK_GL(Pi) is the gray level of pixel i after DPP reduction by the filter of the invention.

2. For the background parts (in FIG. 9C) values after multiplication by a factor, a histogram is also calculated. The minimum and maximum gray levels of this histogram of the calculated data can be extracted: CBKG_GL(min), CBKG_GL(max).

These values can be extracted in any of the mentioned approaches, minimum and maximum gray levels, low percentile (such as 3%) and high percentile (such as 98%), outliers approach, predetermined pixel numbers and so on.

3. Still referring to FIG. 9C, a histogram of ROI 910 is calculated. The minimum and maximum gray levels of this histogram can be extracted: ROI_GL(min), ROI_GL(max).

These values can be extracted in any of the mentioned approaches, minimum and maximum gray levels, low percentile (such as 3%) and high percentile (such as 98%), outliers approach, predetermined pixel numbers and so on.

4. For all CBKG(Pi)<ROI_GL(max) use the transformation:

New_BKG(*Pi*)=Original_BKG(*Pi*)·F where Original_BKG(PI) is the gray level of original pixel i after reducing the DPP and before processing the background data, and New_BKG(Pi) is the newly calculated gray level for this pixel for display in the 8 bit display system.

5. Maximum and minimum values for the unprocessed background image are extracted: BKG_GL(min) and BKG_GL(max).

These values can be extracted in any of the mentioned approaches, minimum and maximum gray levels, low percentile (such as 3%) and high percentile (such as 98%), outliers approach, predetermined pixel numbers and so on.

6. For all CBKG(Pi)≥ROI_GL(max) use the transformation:

New_BKG_GL(*Pi*)=[BKG_GL(*Pi*)-BKG_GL(min)]·*K*+Offset

Where:
Target_GL is the Target gray level; and $$K = \frac{\text{Target\_GL} - \text{ROI\_GL(max)}}{\text{BKG\_GL(max)} - \text{BKG\_GL(min)}}$$

The above description is provided as only one specific example where the background is processed by first degree linear transformations. A more general description of the invention is provided below in a way that enables the use of any monotonic increasing function for transforming the gray level of reduced DPP pixels to the desired gray level:

Step 1. Determine gray levels included in the gray levels range of the ROI part: ROI_GL(min) and ROI_GL(max) where ROI_GL(min)<ROI_GL(max).

Step 2. Determine a Target gray level, Target>ROI_GL(max).

Step 3. Process a first range of pixels of the background. The first range are those pixels that after processing are directed to resemble the unreduced DPP image and will have gray levels that are smaller than ROI_GL(max).

Step 4. For other pixels of the background, the second range, determine gray levels included in the gray levels range of these background pixels: BCK_GL(min) and BKG_GL(max), BCK_GL(min)<BKG_GL(max).

Step 5. Process these pixels so that BCK_GL(min) assumes the value of ROI_GL(max) and BCK_GL(max) assumes the value of the Target gray level.

It should be appreciated that the scope of the invention is not limited to a specific choice of value:

(1) ROI_GL(min) and ROI_GL(max) can be chosen using any method such as the methods below but the invention is not limited to these methods:
  1. Minimum or maximum of the histogram of the ROI part;
  2. Percentile of the histogram of the ROI part;
  3. Minimum or maximum of the histogram of the ROI part after removal of outliers;
  4. Minimum or maximum of the histogram of the ROI part after removal of predetermined number of pixels of highest gray level and removal of predetermined number of pixels of lowest gray level in the histogram of the ROI pixels;
  5. Percentage of the brightest pixel gray level and percentage of the darkest pixel gray level;
  6. Any other method; or
  7. Any combination of the above.

(2) Target gray level can be determined using any method described in (1) above.

(3) For "Process pixels of the background, that after processing are directed to resemble the unreduced DPP image their gray level is smaller than ROI_GL(max)" in step 3 above, is would be appreciated that not only "smaller" can be used but also "equal" or "near" or percentile and other criteria can be used to select the first range of pixels of the background.

(4) For step 4 above, it would be appreciated that BCK_GL(min) and BKG_GL(max), can be determined using any method described in (1) above.

(5) For step 5 above it would be appreciated that the processing of these pixels, using a pixel gray level transformation function, so that BCK_GL(min) assumes the value of ROI_GL(max) and BCK_GL(max) assume the value of the Target gray level can be done with any monotonic increasing function, including but not limited to:
1. a linear function;
2. a polynomial function;
3. a logarithmic function;
4. an exponential function;
5. any other function; or
6. any combination of the above functions.

Figure 9G:
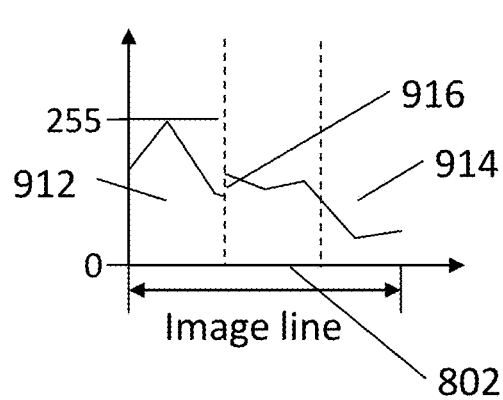
FIG. 9G shows a gray level gap along image line of FIG. 8B that can result from a specific choice of ROI_GL(max), BCK_GL(min) and transformation function.
Figure 9H:
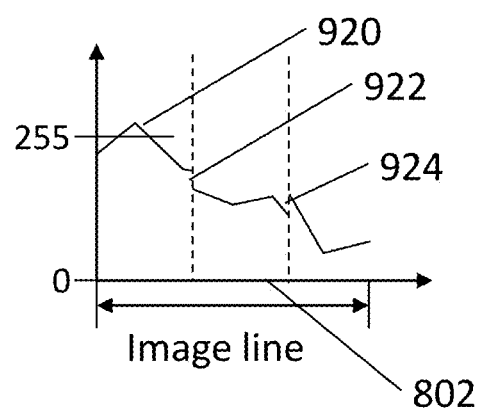
FIG. 9H shows gray level "overshoot" and gaps along the image line of FIG. 8B that can result from a specific choice of ROI_GL(max), BCK_GL(min) and transformation function.

It would be appreciated that with the disclosed scope of selecting gray level values of the above process, additional image results are possible such as shown in FIGS. 9G and 9H.

In FIG. 9G gray level gap 916 along image line 802 can result from a specific choice of ROI_GL(max), BCK_GL(min) and transformation function.

Also in FIG. 9H gray level "overshoot" 920, gaps 922 and 924 along image line 802 can result from a specific choice of ROI_GL(max), BCK_GL(min) and transformation function.

It would also be appreciated that the above image processing can be done whenever the ROI is changed.

It would also be appreciated that the above image processing can be also be performed in real time while the ROI is changing. In such a case, referring to images of a video display, such a process can take place with at least part of the video images captured during motion of the ROI.

In another example of the invention, also the pixels of the ROI part can be processed. Such a processing may, for example, be directed to provide an improved image of the ROI part.

In such a case the ROI part 910 (FIG. 9B) can be processed as desired (for example, change contrast and/or brightness of the image). The background parts 912 and 914 (FIG. 9B) can be processed as described above where the expression "directed to resemble the unreduced DPP" would be in this case: "directed to resemble the unreduced DPP and the processing of ROI part 910".

In another example of the invention, the exposure (amount and spectrum) of x-ray in the ROI is determined to optimize the image of the ROI, for example, for S/N (signal to noise ratio). In this invention such optimization can ignore the background so as to get the optimal exposure in consideration of the ROI alone.

In this approach the handling of the ROI image is made to allocate gray levels range for the second range of the background. The Spare gray level range may be for example 250-255 or in another example 180-255, depending on the user's preferences.

Following such optimization, the background part is processed as described above.

Figure 9I:
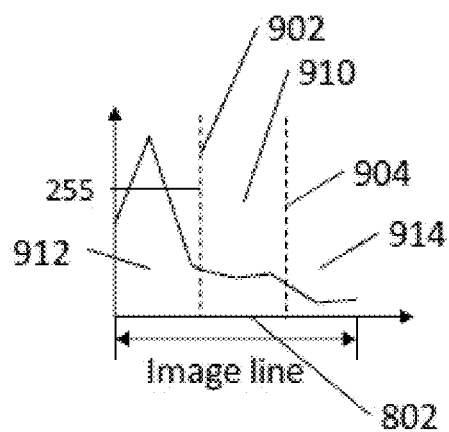
FIG. 9I illustrates a data in image part (ROI) that is dark.
Figure 9J:
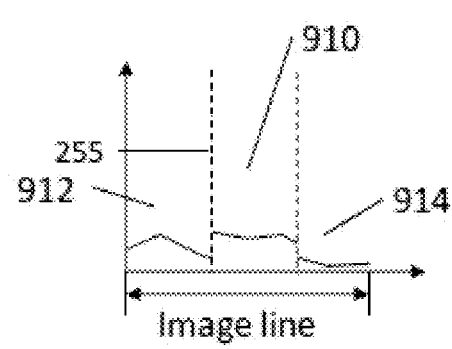
FIG. 9J illustrates the data of FIG. 9I when the filter is used.
Figure 9K:
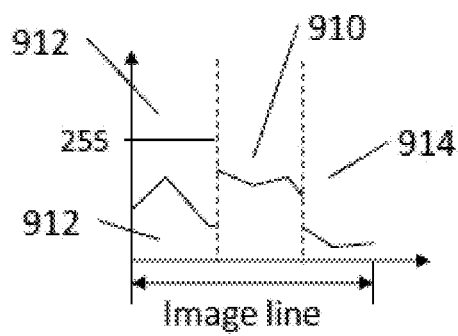
FIG. 9K illustrates the result of increased x-ray intensity relative to FIG. 9J.

This is illustrated in the example of FIGS. 9I-9K.

Figure 9L:
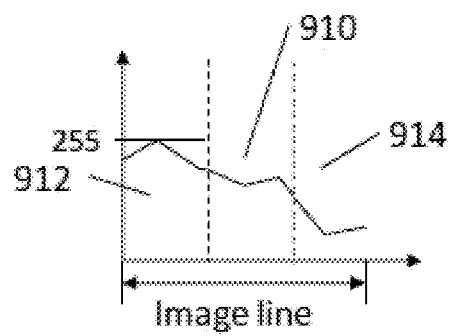
FIG. 9L illustrates image part 910 with improved S/N and image parts 912 and 914 transformed to provide the rest of the image details in a continuous manner of gray levels.

FIG. 9I illustrates a data in image part 910 (ROI) that is dark (compared to image part 910 in FIG. 9A) and therefore has a relatively low S/N value. When the filter is used the intensities will look as illustrated in FIG. 9J. In this example the intensity of the x-ray can be adjusted to provide more radiation. This will typically result in increasing the intensity in all image parts but, particularly in image part 910. FIG. 9K illustrates the result of increased x-ray intensity relative to FIG. 9J. The desired increase in S/N in image part 910 is achieved. The amount of added x-ray is maintained so that pixels of image part 910 will not occupy a range of gray levels above a certain level. This range is saved for the pixels associated with image part 912, the gray level of which is transformed to that range of gray levels using one of the methods described above. The gray levels of the pixels of image part 914 are also transformed using one of the methods described above and the result is illustrated in FIG. 9L providing image part 910 with improved S/N and image parts 912 and 914 transformed to provide the rest of the image details in a continuous manner of gray levels.

The above description provided a detailed disclosure of handling filtered parts 912 and 914 that if transformed to restore gray values as if these parts were not filtered, would have gray values above or below the gray values of image part 910. The example of image line 802 is simplified for the purpose of explanation in the sense that, in FIG. 9A, all unfiltered gray levels of image part 912 are higher than the gray levels of image part 910 and all the gray levels of image part 914 are lower than the gray levels of image part 910. This is not the general case.

In a more general case, pixels outside the ROI, when not filtered, will include pixels of gray values higher than the range of gray values included in the ROI, pixels with gray levels included in the gray level range of the ROI and pixels with gray levels that are lower than the gray level range of the pixels of the ROI.

In a simple approach of handling the filtered part of the image a single value is determined based on the ROI (such as 99% percentile, maximum gray level or any other criteria): GL(ref), a second gray level GL(high) is determined based on the dynamic range of the display system and so that it is larger than GL(ref). Typically, in an 8 bit system not larger than 255 (but can also be larger than 255).

The filtered pixels are divided to at least a first and a second groups. The first group are those pixels with gray levels that, in the non-filtered image or in the filtered image corrected to resemble a non-filtered image, are equal to or larger than GL(ref). The second group are those pixels with gray levels that, in the non-filtered image or in the filtered image corrected to resemble a non-filtered image, are smaller than or equal to GL(ref).

In the first filtered group two values are selected, typically GL1(high) and GL1(low), GL1(high)>GL1(low). These values are selected using any method (such as 99% percentile, maximum gray level or any other criteria). Any of the above described methods is used to transform the gray levels of the first group so that GL1(high)=GL(high) and GL1(low)=GL(ref).

In the second filtered group two values are selected, typically GL2(high) and GL2(low), GL2(high)>GL2(low). These values are selected using any method (such as 99% percentile, maximum gray level or any other criteria). Any of the above described methods is used to transform the gray levels of the second group so that GL2(high)=GL(ref) and GL2(low)<GL(ref).

It would be appreciated that determination of GL(ref) is a useful tool in determination of a constraint to the designated transformation function but it is possible to define the transformation function without selecting GL(ref), for example, a transformation function that asymptotically gets near 255 in an 8 bit system but never assumes this value.

It would be appreciated that the above described methods for determining a gray level and transforming gray levels apply here.

The above description of the present invention was made in reference to image line 802, is applicable to all image lines of the entire image.

In the following example, the description of the invention will be made in reference to an image area. Such an image area might include a section of the entire image or the entire image. Using the terms "image area" or "entire image area" are made for convenience and they refer also to at least one section of the entire image area that is being considered for the purpose of processing while at least one other section might be ignored in reference to the processing.

Reference is made now to FIGS. 11A-11D Representing histograms of at least a part of the image. The horizontal axis represents gray levels of an 8 bit grayscale image (provided as an example) and the vertical axis indicates the number of pixels for each gray level, in the considered part of the image.

Figure 11A:
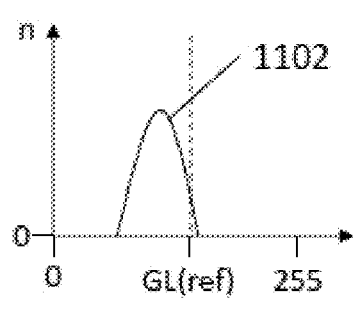
FIGS. 11A-11D represent histograms of at least a part of the image.
Figure 11B:
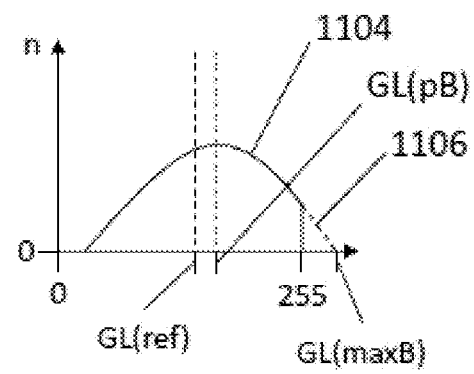

FIG. 11A illustrating histogram 1102 of ROI area 702 of FIG. 7 and FIG. 11B illustrating histogram 1104 of area 704 of FIG. 7 (outside of the ROI) when un-filtered. FIG. 11B illustrates a situation where part of the pixels are in saturation at gray level 255 and the actual physical information illustrated with dashed histogram part 1106 is lost, being all collapsed to gray level 255, resulting in a washed-out image area. GL(maxB) illustrates the maximum gray level of histogram 1104 if not truncated by the 8 bit limitation of maximum gray level 255.

Figure 11C:
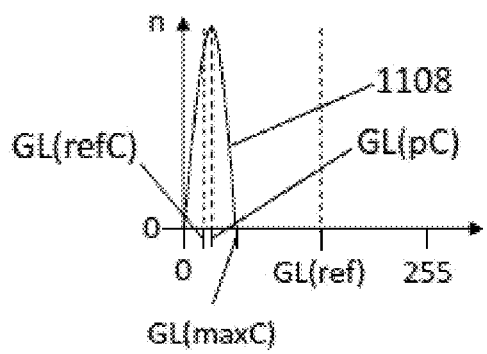

FIG. 11C illustrates the histogram 1108 of area 704 of FIG. 7 (outside of the ROI) when filtered. In this filtered image part, the information that was lost in FIG. 11B is not lost. The maximum gray level of histogram 1108 is GL(maxC).

Histogram 1108 illustrates the result of filtering: the histogram gray level range is compressed towards the left side of the gray scale axis and the number of pixels per gray level increases relative to histogram 1104 reflecting the fact that the same number of pixels is now distributed over a smaller number of gray scales.

As described above, the ROI image part will look as a typical image while the filtered part will look dark relative to the non-filtered ROI image.

In a typical approach to compensate for the dark filtered image, the gray levels of the pixels of FIG. 11C are multiplied by a factor:

$$\frac{GL(maxB)}{GL(maxC)}$$

In another example, the factor can be calculated using the gray levels associated with the peak of the histograms (the gray level with the highest number of pixels). GL(pB) is the gray level of the peak of histogram 1104 of the un-filtered image outside the ROI in FIG. 11B. GL(pC) is the gray level of the peak of histogram 1108 of the filtered image outside the ROI in FIG. 11C.

The factor can now be calculated as:

$$Factor = \frac{GL(pB)}{GL(pC)}$$

Multiplication of the gray levels of the filtered pixels by such factors will restore the image appearance of histogram 1108 as if it was not filtered (histogram 1104) and make the filtered area look similar to the ROI area (with lower gray levels resolution). Secondary effects of filtering such as change in contrast are not discussed here for the benefit of simplified explanation and are brought here by reference as discussed in patent application U.S. Ser. No. 14/380,743.

The problem associated with this approach is that a part of the processed image will require gray levels above 255 and this image part will be truncated as explained in reference to FIG. 11B.

This is solved in the present invention by applying different processing to different parts of the image as described in the example below in reference to the histograms of FIGS. 11A-11D.

A reference gray level, GL(ref), is determined on the basis of the ROI image, for example using histogram 1102 of FIG. 11A.

GL(ref) can be determined using any method, including the methods described above such as the maximum gray level of histogram 1102, a gray level percentile lower than 100% of the pixels in histogram 1102 or higher than 100% of the pixels in histogram 1102, a predetermined gray level offset above or below the maximum gray level of histogram 1102, the maximum of histogram 1102 after removing a predetermined number of the highest gray scale value pixels from the histogram and so on.

With known filtering characteristic the equivalent of GL(ref) is calculated for histogram 1108 of the filtered pixels of FIG. 11C: GL(refC).

Knowing for example that the filtering reduces the gray scale of a pixel to 10% of the same non-filtered pixels:

$$GL(refC)=GL(ref)/10$$

Alternatively, as another example, GL(refC) can be evaluated using GL(pB) and GL(pC):

$$GL(refC) = GL(ref) \cdot \frac{GL(pC)}{GL(pB)}$$

In the present example:
For pixels Pi with GL(Pi)<GL(refC) the following gray level transformation can be applied:

$$New\_GL(Pi)=Original\_GL(Pi) \cdot Factor1$$

Where $$Factor1 = \frac{GL(pB)}{GL(pC)}$$

This will transform the relevant pixels to become similar to the non-filtered pixels of FIG. 11B, for the range of 0≤GL<GL(ref). This range of the histogram is indicated with numerical indicator 1110 in FIG. 11D.

For pixels Pi with GL(Pi)≥GL(refC) the following gray level transformation can be applied:

A Factor2 is calculated:

$$Factor2 = \frac{GL(highD) - GL(ref)}{GL(highC) - GL(refC)}$$

Where:
GL(highD) is determined based on of the dynamic range of the display system, typically between GL(ref) and 255 (in the example 8 bit display system), in any preferred way. It can simply be determined to be 255 or 245 or GL(ref)+(255−GL(ref)·0.9. GL(highD) is preferably a value near 255, preferably lower than or equal to 255 but can also be higher than 255 in an 8 bit display system; and GL(highC) is typically determined between GL(refC) and GL(maxC) in any preferred way. It can simply be determined to be GL(maxC) or GL(maxC)−5 or GL(refC)+(GL(maxC)−GL(refC))·0.9. GL(highC) is preferably a value near GL(maxC), preferably lower than or equal to GL(maxC) but can also be higher than GL(maxC) in an 8 bit display system.

The pixel gray level transformation for pixels Pi with GL(Pi)≥GL(refC) of FIG. 11C can, in this example, be a simple linear transformation $$\text{New\_GL}(Pi) = (\text{Original\_GL}(Pi) - GL(refC)) \cdot \frac{GL(highD) - GL(ref)}{GL(highC) - GL(refC)} + GL(ref)$$

Figure 11D:
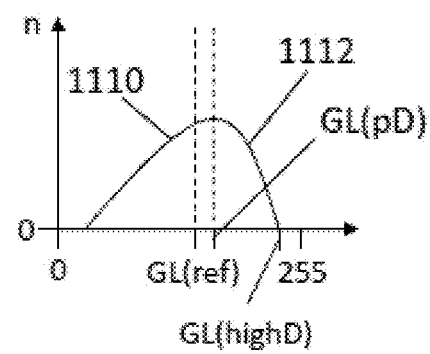

This will result in pixels with new gray levels that result in histogram part 1112 of FIG. 11D, ranging from GL(ref) to, in this example, less than 255.

The saturated data of FIG. 11B is not present in the calculation result of FIG. 11D. Instead the pixels gray level range is compressed for the range above GL(ref) so that all values are within the 256 available gray levels of the system and no washed-out areas are present in the resultant image.

In an even more simple approach, histogram 1108 is simply modified so that it ranges through the entire dynamic range, up to, for example, GL(highD). In such a case the transformation will look like:

$$\text{New\_GL}(Pi) = \text{Original\_GL}(Pi) \cdot \frac{GL(highD)}{GL(maxC)}$$

It would be appreciated that the processing of these pixels can be done with any monotonic increasing function, including but not limited to:
 (1) a linear function;
 (2) a polynomial function;
 (3) a logarithmic function;
 (4) an exponential function;
 (5) any other function; or
 (6) any combination of the above functions.

All such transformations are preferably monotonic increasing functions.

It would also be appreciated that the examples above do not limit the scope of the invention and that the examples are specific implementation of processing an image of an x-ray system comprising an x-ray source, at least one partially transparent x-ray filter, an x-ray detector, a monitor to display x-ray images detected by said detector and image processing means, a method of generating an x-ray image and modifying said image for display comprising:
 using said at least one filter to filter x-ray so as to reduce x-ray intensity in at least one part of the image;
 maintaining at least one part of the image un-filtered;
 determining a first gray level based on at least one unfiltered part of the image;
 modifying at least a first plurality of pixels of the filtered image part using a first gray level transformation function, wherein gray levels of the modified first plurality of pixels are equal to or lower than said first gray level; and
 modifying at least a second plurality of pixels of the filtered image part using a second gray level transformation function, wherein the gray levels of the modified second plurality of pixels are higher than or equal to said first gray level.

An alternative phrasing would be: using a first gray level transformation function to transform (or map) the gray levels of a first plurality of pixels of the filtered image part to a gray level that is equal to or lower than said first gray level; and
 using a second gray level transformation function to transform (or map) the gray levels of a second plurality of pixels of the filtered image part to a gray level that is higher than or equal to said first gray level. This alternative phrasing applies to all relevant invention parts.

In an additional approach, while the image part included in the ROI is maintained unchanged, the dynamic range of image part outside the ROI is modified to occupy a predetermined range of the display dynamic range.

In yet another approach, the dynamic range of the image part included in the ROI is modified to occupy a first predetermined range of the display dynamic range and the dynamic range of image part outside the ROI is also modified to occupy a second predetermined range of the display dynamic range. The first and second predetermined ranges of the display dynamic range can be selected to be identical.

It would be appreciated that sometimes also pixel-location dependent correction is desired. Such an example is pixel non-uniformity correction resulting from the x-ray detector non-uniform response to x-ray radiation at different locations of the detector. Another example is vignetting of the optical system typically used in conjunction with image intensifier x-ray detectors (but also present to a certain degree in flat panel detectors, due to the point-source nature of x-ray radiation in x-ray tubes. In such cases, the gray levels of the pixels of the first plurality of pixels (for example) are also modified based on location. Therefore, in addition to aiming at a range equal to or lower than said first gray level, the first gray level transformation function may vary from pixel to pixel of the first plurality of pixels, to provide not only the aiming at a range equal to or lower than said first gray level, but also to provide a correction that is pixel-location dependent, such as pixel non-uniformity and vignetting.

Therefore, the scope of the invention is not limited by additional considerations of pixel correction and it includes:
 modifying at least one first pixel of the filtered image part using a first gray level transformation function, wherein the gray level of the modified at least one first pixel is equal to or lower than said first gray level; and
 modifying at least one second pixel of the filtered image part using a second gray level transformation function, wherein the gray level of the modified at least one second pixel is higher than or equal to said first gray level.

In alternative phrasing:
 using at least one first gray level transformation function to transform (or map) the gray level of at least one first pixel of the filtered image part to a gray level that is equal to or lower than said first gray level; and
 using at least one second gray level transformation function to transform (or map) the gray level of at least one second pixel of the filtered image part to a gray level that is higher than or equal to said first gray level.

This alternative phrasing applies to all relevant invention parts.

In another example, determining a first gray level based on at least one unfiltered part of the image;

determining a second gray level based on the dynamic range of the display system;

using at least one first gray level transformation function to transform the gray level of at least one first pixel of the filtered image part to a gray level that is equal to or lower than said first gray level; and using at least one second gray level transformation function to transform the gray level of at least one second pixel of the filtered image part to a gray level that is higher than or equal to said first gray level and lower than or equal to said second gray level.

In the explanation below, the term "image" is used mainly to refer to the content of a frame but sometimes, depends on the context, "image" and "frame" might be the same thing. Typically a frame contains an image as received from the multiple frames imaging system. It might include image processing or be raw image, as received from the x-ray detector.

It would be appreciated that the above transformations can be calculated and optimized for each frame of a multiple frame system. Yet, if the image changes frequently, depending on the object nature, such frame by frame processing might provide ever changing brightness and contrast appearance in the image and become annoying to the user.

This can be overcome in a number of ways directed to trace the sequential stream of multiple frames provided by the multiple frame imaging device in order to detect a level of change in the images sequence, based on preferred criteria. When such a level of change is identified a re-determination takes place of at least one item such as a gray level transformation function, GL(ref), GL(maxB), GL(refC), GL(pC), GL(pD) and GL(highD).

Following are few examples for specific implementation of the invention:

(1) Check the histogram of the entire FOV, or of a part of the image (as it would be with a correction to restore the image pixels to the gray level expected without a filter) and evaluate the brighter pixels (the bright part of the image, such as the higher percentile pixels, for example percentile in the range 50%-100%). Keep a fixed processing until receiving a frame with a gray level change in the brighter pixels that is above a predetermined threshold or below the same or another predetermined threshold and following such a condition, re-determine at least one of the above items, and use the currently determined set of items for frames processing until a change larger than a threshold is detected again.

(2) Check the histogram of the entire FOV, or of a part of the image, as it would be with a correction to restore the image pixels to the gray level expected without a filter and evaluate the brighter pixels (such as the higher percentile pixels) for multiple frames. The number of frames could be determined or a time period can be determined to select the frames. For example: 10 last frames or the frames of the 5 last seconds. Another example: 10 frames before the last 5 frames or the frames of the 5 seconds before the last 2 seconds. Adjust the processing for the frame of the largest dynamic range (ratio between the average gray level of the high percentile pixels to the gray level average of the lower percentile pixels). Adjust the processing for the histogram of that frame. This can also be done using more than one frame, for example averaging n frames of the largest dynamic range. Optimize the processing for the histogram of that average frame.

(3) Same as 2 but, to clarify one version of 2, the search for the frame with the largest dynamic range is made for m last frames, therefore the larger dynamic range may increase or decrease while frames are generated.

(4) Same as 3 but the search is for n frames of the largest dynamic range within the last m frames, m>n and these n frames are averaged to provide the histogram of the dynamic range for processing.

(5) Same as above using weighted average (WA) of past frames, in one example:

$$WA(1) = \text{Image}(1)$$

For $n > 1$ $$WA(n) = \frac{WA(n-1) + \text{image}(n) \cdot K}{1 + K}$$

Where:
WA is the weighted average;
Image(1) is the first image in a series of images;
Image(n) is the nth image in a series of images; and
K is a factor, $0 \leq K$, selectable by the user. The larger K is the more the latest image dominates WA and the histogram of WA thereby.

It would be appreciated that not every image of the image sequences must be used and that any subset of images can be used, for example, only every $3^{rd}$ image can be used such that n belongs to the set of integers $\{1, 4, 7, 10, \ldots\}$ and if, in this example n=7 then n−1 in the equation above means 4.

(6) Same as example 5 including a reset feature: When the latest image varies from WA more than a threshold, the WA calculation is reset and starts again from the latest image. Variation of more than a threshold concepts of this invention were described above.

It would be appreciated, for all the above examples and for the invention itself, that not every image of the image sequences must be used to re-determine the above items and that any subset of images can be used, for example, only every $3^{rd}$ image can be used such that n belongs to the set of integers $\{1, 4, 7, 10, \ldots\}$ Although the above description provided as a saturation example the 256 gray levels of an 8 bit system it would be appreciated that the saturation phenomenon is completely analogous in systems of other number of image pixel bits (such as 10 bit, 12 bit and 16 bit systems) and it is also analogous to detector saturation that might happen at a gray level below the imaging system maximum gray level. In such a case the sensor saturation (and the invention description thereby) is completely analogous by considering the maximum gray level of the imaging system as the gray level where the detector becomes saturated.

It would be appreciated that the above examples are provided to enhance the explanation of the invention and are not limiting features of the invention. The scope of the invention includes analyzing the last frame to generate the desired transformation but it covers also the usage of any set or a subset of earlier frames for the analysis made to generate the desired transformation.

It would also be appreciated that the terms tone reproduction, transformation function and gray level transformation function are used equivalently in the disclosed description.

The image enhancement methods according to the present invention may be applied both in real-time, where the user attention currently is, but also for preparing the acquisitions of images with ROI based resolution selectivity for future post processing (cine, storage, transmission etc.) based on user designated ROIs for future processing needs, where image processing may also be based on stored history of ROIs and their trajectories as well as image segmentation labels, tools trajectories history, anatomy and procedure know how and knowledge base. For example, when a site (identified either via pixel address or via labeled anatomy) is visited frequently, it may need enhancement beyond a simple non-ROI pixel etc. The stored images may be projected in a cine-loop mode that allows scrolling back through the preceding several seconds frame by frame.

Similarly, when using DynaCT® for obtaining computed tomography (CT)-like images using a C-arm system, the user/operator may identify images to be saved for future uses. Identification of images may be done automatically, using for example an eye-tracking device, or manually by the operator selecting images using an input device, which may comprise touch (keyboard, screen), audio (microphone), etc.

It would be appreciated that the invention is not limited to 8 bit display system and this system is used only as an example to facilitate the description of the invention.

All the examples above use specific values for the sake of example and simple description.

It would be appreciated that 90% histogram percentile can be replaced by the brightest pixel (pixel of maximum gray level) that is equivalent to 100% percentile, by an outliers (such as in statistics, an outlier is an observation point that is distant from other observations) ignoring outlier pixels in the histogram or by ignoring a fixed number of the brightest pixels instead of using percentile.

It would also be appreciated that the target number (such as in the examples of GL(high) and GL(highD) may be below the maximum displayable gray level (such as 225 out of 255 in the above example), or it might be the maximum displayable gray level or above the maximum displayable gray level. All depends on the desired user experience and thereby on the specific implementation.

Therefore, all the examples above are not limited to the specific values used and the scope of the invention includes other possibilities as explained.

It would be appreciated by those skilled in the art that the above described methods and technologies are not limited to the configurations and methods mentioned herein above as examples. These are provided as examples and other configurations and methods can be used to optimize final result, depending on the specific design and the set of technologies implemented in the production of the design.

The herein above embodiments are described in a way of example only and do not specify a limited scope of the invention.

The scope of the invention is defined solely by the claims provided herein below:

The invention claimed is:

1. An x-ray system comprising an x-ray source, at least one partially transparent x-ray filter, an x-ray detector, a monitor to display x-ray images detected by said detector and image processing means, wherein said display comprises a dynamic range;
    said system configured to generate at least one x-ray image and modify at least one of said at least one image for display by:
    using said at least one filter to filter x-ray so as to reduce x-ray intensity in at least one part of said image;
    maintaining at least one part of said image unfiltered by said at least one filter;
    determining a range in said dynamic range of said display; and
    modifying at least one pixel in said at least one filtered part of said image based on said determined range of said dynamic range of said display;
    wherein said modification results in a pixel value that is inside said dynamic range of said display.

2. The system of claim 1, wherein said modification is made by at least one gray level transformation function selected from the group consisting of:
    (1) a linear function;
    (2) a polynomial function;
    (3) a logarithmic function;
    (4) an exponential function; and
    (5) any combination of the above functions.

3. The system of claim 1, wherein a first gray level is determined based on said unfiltered image; and
    a second gray level is determined based on said filtered image;
    said at least one pixel of said filtered image is transformed by a transformation so that said second gray level is changed relative to said first gray level; and
    said transformation maintains the gray levels of said filtered image within said determined range of said dynamic range of said display.

4. The system of claim 3, wherein the difference between said first gray level and said second gray level after said transformation is less than 25% of said determined range of said dynamic range of said display.

5. A method of modifying dynamic range of an image, comprising:
    providing an x-ray system comprising an x-ray source, at least one partially transparent x-ray filter, an x-ray detector, a monitor to display x-ray images detected by said detector and image processing means, wherein said display comprises a dynamic range;
    generating at least one x-ray image and modifying at least one of said at least one image for display by:
    using said at least one filter to filter x-ray so as to reduce x-ray intensity in at least one part of said image;
    maintaining at least one part of said image unfiltered by said at least one filter;
    determining a range in said dynamic range of said display; and
    modifying at least one pixel in said at least one filtered part of said image based on said determined range of said dynamic range of said display,
    wherein said modification results in a pixel value that is inside said dynamic range of said display.

6. The method of claim 5, wherein said modification is made by at least one gray level transformation function selected from the group consisting of:
    (1) a linear function;
    (2) a polynomial function;
    (3) a logarithmic function;
    (4) an exponential function; and
    (5) any combination of the above functions.

7. The method of claim 5, further comprising:
    determining a first gray level based on said unfiltered image; and
    determining a second gray level based on said filtered image;
    transforming by a transformation said at least one pixel of said filtered image so that said second gray level is changed relative to said first gray level; and maintaining the gray levels of said filtered and unfiltered images within their corresponding said determined ranges of said dynamic range of said display.

8. The method of claim 7, wherein the difference between said first gray level and said second gray level after said transformations is less than 25% of said dynamic range of said display.

* * * * *